US010023622B2

(12) United States Patent  
Härd et al.

(10) Patent No.: US 10,023,622 B2
(45) Date of Patent: Jul. 17, 2018

(54) METHOD OF IMMUNIZATION FOR REDUCING TOXIC DAMAGED CAUSED BY OLIGOMERIC FORM OF THE AMYLOID-BETA PROTEIN WITH STABLE AMYLOID BETA MONOMERS AND OLIGOMERS

(71) Applicants: Torleif Härd, Uppsala (SE); Anders Sandberg, Gothenburg (SE)

(72) Inventors: Torleif Härd, Uppsala (SE); Anders Sandberg, Gothenburg (SE)

(73) Assignee: ALZINOVA AB, Gothenburg (SE)

( * ) Notice: Subject to any disclaimer, the term of this patent is extended or adjusted under 35 U.S.C. 154(b) by 0 days.

(21) Appl. No.: 15/599,906

(22) Filed: May 19, 2017

(65) Prior Publication Data

US 2018/0030103 A1 Feb. 1, 2018

Related U.S. Application Data

(62) Division of application No. 12/937,379, filed as application No. PCT/SE2009/050378 on Apr. 14, 2009, now Pat. No. 9,688,734.

(30) Foreign Application Priority Data

Apr. 14, 2008 (SE) ........................................ 0800842
Nov. 20, 2008 (SE) ........................................ 0802433

(51) Int. Cl.
*A61K 38/00* (2006.01)
*C07K 14/00* (2006.01)
*G01N 33/53* (2006.01)
*C07K 14/47* (2006.01)

(52) U.S. Cl.
CPC .......... *C07K 14/4711* (2013.01); *A61K 38/00* (2013.01); *G01N 2800/2821* (2013.01); *G01N 2800/52* (2013.01)

(58) Field of Classification Search
CPC .......... A61K 2039/505; A61K 39/0007; A61K 39/0005; A61K 39/6031; A61K 2300/00; A61K 39/00; A61K 47/4833; A61K 47/48284; A61K 2039/55516; A61K 38/00; A61K 38/10; G01N 33/6896; G01N 2800/2821; G01N 2333/4709; C07K 2317/34; C07K 2317/24; C07K 2317/565; C07K 2317/56; C07K 7/06
See application file for complete search history.

(56) References Cited

U.S. PATENT DOCUMENTS 7,589,168 B2 * 9/2009 Paris .................. A61K 38/1709
530/300
2004/0250302 A1 * 12/2004 Lowe .................. A01K 67/0339
800/8

2006/0018918 A1 1/2006 Chang
2006/0079447 A1 * 4/2006 Wetzel .............. A61K 31/4164
514/1.1
2007/0021345 A1 1/2007 Gazit
2007/0213512 A1 9/2007 Krafft
2011/0092445 A1 * 4/2011 Barghorn ........... C07K 14/4711
514/21.1

FOREIGN PATENT DOCUMENTS

| JP | 659933 | 2/2010 |
|----|--------|--------|
| WO | 2003/014329 | 2/2003 |
| WO | 2004067561 A | 8/2004 |
| WO | 2005089539 A1 | 9/2005 |
| WO | 2007005358 A | 1/2007 |
| WO | 2007005359 A | 1/2007 |
| WO | 2007142320 A | 12/2007 |
| WO | 2010/011947 A2 | 1/2010 |

OTHER PUBLICATIONS

Anger. Neurotoxicology 1991. 12: 403-13.*
Tayebati. Mech. Ageing Dev. 2006. 127: 100-8.*
Sarter. Neurosci. and Biobehav. Rev. 2004. 28: 645-650.*
Hoke et al. Nat. Clin. Pract. Neurol. 2006: 448-454.*
Otvos et al. Curr. Protein and Peptide Sci., 2002; 3:643-652.*
Moore et al. Annu. Rev. Neurosci. 2005; 28: 57-87.*
International Search Report (dated Jul. 3, 2009); Written Opinion of International Search Authority (dated Jul. 3, 2009); Written Opinion of the International Preliminary Examining Authority (dated Apr. 9, 2010); International Preliminary Report on Patentability (dated Jul. 29, 2010).
Blennow, K., et ah, Lancet 368: 387-403 (2006).
Dobson, C. M., Protein Pept. Lett. 13: 219-227 (2006).
Haass, C. and Selkoe D. J., Nature Reviews Mol. Cell. Biol. 8: 101-112 (2007).
Glabe, C. G., Trends Biochem. Sci. 29: 542-547 (2004).
Lomakin, A., et ah, Proc. Natl. Acad. Sci. USA 93: 1125-1129 (1996).
Shivaprasad, S. and Wetzel, R., Biochemistry 43: 153-15317 (2004).
Netzel, R., et al, Biochemistry 46: 1-10 (2007).
Hoyer, W. et al, Proc. Natl. Acad. Sci. USA. 105: 5099-5104 (2008).
Petkova, A. T., et al, Biochemistry 45: 498-512.
Kang, J., et ah, Nature 325: 773-776 (1987).

(Continued)

*Primary Examiner* — Chang-Yu Wang
(74) *Attorney, Agent, or Firm* — Jeffrey S. Melcher; Manelli Selter PLLC

(57) ABSTRACT

The invention provides monomeric and oligomeric amyloid beta peptide isomers that are resistant towards fibrillogenesis and their use as screening reagents or antigens in methods and pharmaceutical preparations for the treatment of Alzheimer's disease and other conditions related to protein misfolding. The invention further provides transgenic animals expressing modified amyloid precursor proteins or amyloid beta peptides.

9 Claims, 15 Drawing Sheets

(56) References Cited

OTHER PUBLICATIONS

Clarke, J., and Fersht, A., Biochemistry 32: 4322-4329 (1993).
Butterfield, D. A., and Kanski, I, Peptides 23: 1299-1309 (2002).
Stine, W. B. et al. J. Biol. Chem. 278: 11612-11622 (2003).
Lee, E. K., et al, Prot. Expr. Purif. 40:183-189 (2005).
Grönwall, C, et al, J. Biotechnol. 128: 162-183 (2007).
Walsh, D. M., et al., J. Biol. Chem. 274: 25945-25952 (1999).
Crowther, D. C. et al. (2005) Neuroscience 132: 123-135.
Caenorhabditis elegans (Link, CD. (1995) Proc. Natl. Acad. Sci. USA 92: 9368-9372.
Gene Targeting: A Practical Approach, Joyner, ed., Oxford University Press, Inc. (2000).
Jaenich, R. (1976) Proc. Natl. Acad. Sci. USA 73:1260-1264.
Manipulating the Mouse Embryo, Hogan eds., Cold Spring Harbor Laboratory Press, Cold Spring Harbor, 1986.
Jahner et al. (1985) Proc. Natl. Acad. Sci. USA 82:6927-6931.
Van der Putten et al. (1985) Proc. Natl. Acad. Sci. USA 82:6148-6152.
Stewart et al (1987) Embo J. 6:383-388.
Jahner et al. (1982) Nature 298:623-628.
Levine, H., Methods Enzymol. 309: 274-284 (1999).
DeLellis, R. A., et al, J. Histochem. Cvtochem. 16: 663-665 (1968).
Walsh, D. M., et al, J. Biol. Chem. 272: 22364-22372 (1997).
Hou, L., et ah, J. Am. Chem. Soc. 126: 1992-2005 (2003).
Japanese Office Action issued in Japanese Application No. 2011-503942, pp. 1-4 dated Oct. 15, 2013.
Kayad,"Common structure of Soluble Amyloid Oligomers Implies Common Mechanism of Pathogenesis," Apr. 16, 2003, vol. 300 Science. pp. 486-489.
International Search Report (dated Jul. 3, 2009); Written Opinion of International Search Authority (dated Jul. 3, 2009); Written Opinion of the International Preliminary Examining Authority (dated Apr. 9, 2010); International Preliminary Report on Patentability (dated Jul. 29, 2010), issued in PCT/SE2009/050378, pp. 1-14.
Wetzel, R., et al, Biochemistry 46: 1-10 (2007).
Petkova, A. T., et al, Biochemistry 45: 498-512 (2006).
Link, Caenorhabditis elegans (1995) Proc. Natl. Acad. Sci. USA 92: 9368-9372.
European Search Report issued in European patent application No. 09732855.3, dated Mar. 25, 2012, pp. 1-6.
Lambert, Diffusible, nonfibrillar ligands derived from AB1-42 are potent central nervous system neurotoxins, Proc. Natl. Acad. Sci. USA, vol. 95, pp. 6448-6453, May 1998.
Notification of reasons for refusal issued in Japanese Patent Application No. 2011-503942, dated Oct. 2, 2013, pp. 1-4.
Lendel, "A hexameric peptide barrel as building block of amyloid-B protofibrils," Agnew. Chem. Int. Ed, 2014, 53, 1-6.
Sandberg, Stabilization of neurotixic alzheimer amyloid-B oligomers by protein engineering, www.pnas.org/cgi/doi/10.1073/pnas.1001740107, PNAS, Aug. 31, 2010, vol. 107, No. 35, pp. 15595-15600.
Extended European Search Report dated Mar. 26, 2012.
Sandberg, "Stabilization of Neurotoxic Alzheimer amyloid-oligomers by protein engineering," Proceedings of the National Academy of Sciences, vol. 107, No. 35, Aug. 31, 2010, pp. 15595-15600.
Shivaprasad, Shivaprasad (I), Methods in Enzymology, 2006, 413: 182-198.
Shivaprasa, Shivaprasad (II), J. Biol. Chem. 2006, 281,: 993-1000.
Burges, J of Cell Bio. 1990, 111:2129-2138.
Bowie, Science, 1990, 247:1306-1310.
Pawson, 2003, Science 300:445-452.

\* cited by examiner

SEQUENCE LISTING

```
<160> NUMBER OF SEQ ID NOS: 16

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 40
<212> TYPE: PRT
<213> ORGANISM: Artificial Sequence
<220> FEATURE:
<223> OTHER INFORMATION: Sequence derived from human amyloid beta

<400> SEQUENCE: 3

Asp Ala Glu Phe Arg His Asp Ser Gly Tyr Glu Val His His Gln Lys
1               5                   10                  15

Leu Val Phe Phe Cys Glu Asp Val Gly Ser Asn Lys Gly Cys Ile Ile
            20                  25                  30

Gly Leu Met Val Gly Gly Val Val
        35                  40

<210> SEQ ID NO 4
```

<211> LENGTH: 42
<212> TYPE: PRT
<213> ORGANISM: Artificial Sequence
<220> FEATURE:
<223> OTHER INFORMATION: Sequence derived from human amyloid beta

<400> SEQUENCE: 4

Asp Ala Glu Phe Arg His Asp Ser Gly Tyr Glu Val His His Gln Lys
1               5                   10                  15

Leu Val Phe Phe Cys Glu Asp Val Gly Ser Asn Lys Gly Cys Ile Ile
            20                  25                  30

Gly Leu Met Val Gly Gly Val Val Ile Ala
        35                  40

<210> SEQ ID NO 5
<211> LENGTH: 42
<212> TYPE: PRT
<213> ORGANISM: Artificial Sequence
<220> FEATURE:
<223> OTHER INFORMATION: Sequence derived from human amyloid beta

<400> SEQUENCE: 5

Asp Ala Glu Phe Arg His Asp Ser Gly Tyr Glu Val His His Gln Lys
1               5                   10                  15

Leu Val Phe Phe Cys Gly Asp Val Gly Ser Asn Lys Gly Cys Ile Ile
            20                  25                  30

Gly Leu Met Val Gly Gly Val Val Ile Ala
        35                  40

<210> SEQ ID NO 6
<211> LENGTH: 42
<212> TYPE: PRT
<213> ORGANISM: Artificial Sequence
<220> FEATURE:
<223> OTHER INFORMATION: Sequence derived from human amyloid beta

<400> SEQUENCE: 6

Asp Ala Glu Phe Arg His Asp Ser Gly Tyr Glu Val His His Gln Lys
1               5                   10                  15

Leu Val Phe Phe Cys Gln Asp Val Gly Ser Asn Lys Gly Cys Ile Ile
            20                  25                  30

Gly Leu Met Val Gly Gly Val Val Ile Ala
        35                  40

<210> SEQ ID NO 7
<211> LENGTH: 42
<212> TYPE: PRT
<213> ORGANISM: Artificial Sequence
<220> FEATURE:
<223> OTHER INFORMATION: Sequence derived from human amyloid beta

<400> SEQUENCE: 7

Asp Ala Glu Phe Arg His Asp Ser Gly Tyr Glu Val His His Gln Lys
1               5                   10                  15

Leu Val Phe Phe Cys Glu Asn Val Gly Ser Asn Lys Gly Cys Ile Ile
            20                  25                  30

Gly Leu Met Val Gly Gly Val Val Ile Ala
        35                  40

<210> SEQ ID NO 8
<211> LENGTH: 42
<212> TYPE: PRT
<213> ORGANISM: Artificial Sequence -continued
<220> FEATURE:
<223> OTHER INFORMATION: Sequence derived from human amyloid beta

<400> SEQUENCE: 8

Asp Ala Glu Phe Arg His Asp Ser Gly Tyr Glu Val His His Gln Lys
1               5                   10                  15

Leu Val Phe Phe Cys Lys Asp Val Gly Ser Asn Lys Gly Cys Ile Ile
            20                  25                  30

Gly Leu Met Val Gly Gly Val Val Ile Ala
        35                  40

<210> SEQ ID NO 9
<211> LENGTH: 34
<212> TYPE: PRT
<213> ORGANISM: Artificial Sequence
<220> FEATURE:
<223> OTHER INFORMATION: Sequence derived from human amyloid beta

<400> SEQUENCE: 9

Gly Tyr Glu Val His His Gln Lys Leu Val Phe Phe Cys Glu Asp Val
1               5                   10                  15

Gly Ser Asn Lys Gly Cys Ile Ile Gly Leu Met Val Gly Gly Val Val
            20                  25                  30

Ile Ala

<210> SEQ ID NO 10
<211> LENGTH: 42
<212> TYPE: PRT
<213> ORGANISM: Artificial Sequence
<220> FEATURE:
<223> OTHER INFORMATION: Sequence derived from human amyloid beta

<400> SEQUENCE: 10

Ser Asp His Arg Phe Glu Ala Asp Gly Tyr Glu Val His His Gln Lys
1               5                   10                  15

Leu Val Phe Phe Cys Glu Asp Val Gly Ser Asn Lys Gly Cys Ile Ile
            20                  25                  30

Gly Leu Met Val Gly Gly Val Val Ile Ala
        35                  40

<210> SEQ ID NO 11
<211> LENGTH: 770
<212> TYPE: PRT
<213> ORGANISM: Homo sapiens

<400> SEQUENCE: 11

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

```
Ile Pro Tyr Arg Cys Leu Val Gly Glu Phe Val Ser Asp Ala Leu Leu
            115                 120                 125
Val Pro Asp Lys Cys Lys Phe Leu His Gln Glu Arg Met Asp Val Cys
        130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
        195                 200                 205
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Thr Glu Ser Val Glu Glu Val Val Arg
        275                 280                 285
Glu Val Cys Ser Glu Gln Ala Glu Thr Gly Pro Cys Arg Ala Met Ile
290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
        355                 360                 365
Ala Ser Thr Pro Asp Ala Val Asp Lys Tyr Leu Glu Thr Pro Gly Asp
370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
        435                 440                 445
Glu Arg Gln Gln Leu Val Glu Thr His Met Ala Arg Val Glu Ala Met
450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
            500                 505                 510
Glu His Val Arg Met Val Asp Pro Lys Lys Ala Ala Gln Ile Arg Ser
        515                 520                 525
```

Gln Val Met Thr His Leu Arg Val Ile Tyr Glu Arg Met Asn Gln Ser
        530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
            595                 600                 605

Val Asn Gly Glu Phe Ser Leu Asp Asp Leu Gln Pro Trp His Ser Phe
        610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
                660                 665                 670

Ala Glu Phe Arg His Asp Ser Gly Tyr Glu Val His His Gln Lys Leu
            675                 680                 685

Val Phe Phe Cys Glu Asp Val Gly Ser Asn Lys Gly Cys Ile Ile Gly
        690                 695                 700

Leu Met Val Gly Gly Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
                740                 745                 750

Gln Gln Asn Gly Tyr Glu Asn Pro Thr Tyr Lys Phe Phe Glu Gln Met
            755                 760                 765

Gln Asn
    770

<210> SEQ ID NO 12
<211> LENGTH: 770
<212> TYPE: PRT
<213> ORGANISM: Homo sapiens

<400> SEQUENCE: 12

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

```
Val Pro Asp Lys Cys Lys Phe Leu His Gln Glu Arg Met Asp Val Cys
    130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
        195                 200                 205
Trp Trp Gly Gly Ala Asp Thr Asp Tyr Ala Asp Gly Ser Glu Asp Lys
    210                 215                 220
Val Val Glu Val Ala Glu Glu Glu Val Ala Glu Val Glu Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Thr Glu Ser Val Glu Glu Val Val Arg
        275                 280                 285
Glu Val Cys Ser Glu Gln Ala Glu Thr Gly Pro Cys Arg Ala Met Ile
    290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
        355                 360                 365
Ala Ser Thr Pro Asp Ala Val Asp Lys Tyr Leu Glu Thr Pro Gly Asp
    370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
        435                 440                 445
Glu Arg Gln Gln Leu Val Glu Thr His Met Ala Arg Val Glu Ala Met
    450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
            500                 505                 510
Glu His Val Arg Met Val Asp Pro Lys Lys Ala Ala Gln Ile Arg Ser
        515                 520                 525
Gln Val Met Thr His Leu Arg Val Ile Tyr Glu Arg Met Asn Gln Ser
    530                 535                 540
```

```
Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
770

<210> SEQ ID NO 13
<211> LENGTH: 5
<212> TYPE: PRT
<213> ORGANISM: Artificial Sequence
<220> FEATURE:
<223> OTHER INFORMATION: Sequence derived from human amyloid beta

<400> SEQUENCE: 13

Leu Val Phe Phe Cys
1               5

<210> SEQ ID NO 14
<211> LENGTH: 7
<212> TYPE: PRT
<213> ORGANISM: Artificial Sequence
<220> FEATURE:
<223> OTHER INFORMATION: Sequence derived from human amyloid beta

<400> SEQUENCE: 14

Cys Ile Ile Gly Leu Met Val
1               5

<210> SEQ ID NO 15
<211> LENGTH: 8
<212> TYPE: PRT
<213> ORGANISM: Artificial Sequence
<220> FEATURE:
<223> OTHER INFORMATION: Sequence derived from human amyloid beta
```

```
<400> SEQUENCE: 15

Glu Asp Val Gly Ser Asn Lys Gly
1               5

<210> SEQ ID NO 16
<211> LENGTH: 20
<212> TYPE: PRT
<213> ORGANISM: Artificial Sequence
<220> FEATURE:
<223> OTHER INFORMATION: Sequence derived from human amyloid beta

<400> SEQUENCE: 16

Leu Val Phe Phe Cys Glu Asp Val Gly Ser Asn Lys Gly Cys Ile Ile
1               5                   10                  15

Gly Leu Met Val
            20
```

METHOD OF IMMUNIZATION FOR REDUCING TOXIC DAMAGED CAUSED BY OLIGOMERIC FORM OF THE AMYLOID-BETA PROTEIN WITH STABLE AMYLOID BETA MONOMERS AND OLIGOMERS

FIELD OF THE INVENTION

The invention relates to monomeric and oligomeric amyloid beta peptides that are resistant towards fibrillogenesis for use as antigens or screening reagents for the treatment of Alzheimer's disease and other conditions related to protein misfolding.

BACKGROUND OF THE INVENTION

Alzheimer's disease (AD) is an age-related neurodegenerative disease characterized by the accumulation of insoluble amyloid deposits of the amyloid-β (Aβ) protein generated by the cleavage of the amyloid precursor protein (APP) (Blennow, K., et al., Lancet 368: 387-403 (2006)). AD is one of several diseases caused by protein misfolding, which includes over 22 other known ailments such as Parkinson's disease and Type II diabetes (Dobson, C. M., Protein Pept. Lett. 13: 219-227 (2006)). There are at present no effective treatments against AD and most of the other protein misfolding diseases, partly owing to the fact that it is still unclear if and how these deposits are toxic. In fact, focus has recently shifted away from the insoluble amyloid deposits, which previously were believed to be the cause of AD, towards soluble Aβ oligomeric species as the toxic agent (Haass, C. and Selkoe D. J., Nature Reviews Mol. Cell. Biol. 8: 101-112 (2007)). In addition, conformation-dependent antibodies raised against Aβ oligomers (e.g. the polyclonal A11 antibody) have shown to be reactive towards other oligomeric species in addition to Aβ, thus suggesting that these toxic structures are generic in the protein misfolding diseases although different proteins are involved (Glabe, C. G., Trends Biochem. Sci. 29: 542-547 (2004)). Much effort is therefore currently being focused worldwide on the isolation and characterization of such soluble oligomers for drug-screening and immunogenic purposes. However, both monomeric and oligomeric Aβ proteins have a high tendency to aggregate further into fibrils. This fibrillation is a spontaneous nucleation-dependent polymerization reaction for which the rate is sensitive to peptide concentration (Lomakin, A., et al., Proc. Natl. Acad. Sci. USA 93: 1125-1129 (1996)). In consequence, fibrillogenesis seriously limits the longevity of the oligomeric preparations, and also the concentrations at which they can be kept.

The wild-type Aβ protein implicated in AD is a very fibrillation prone peptide at concentrations>100 μM. At lower concentrations (>20 μM to <100 μM) said protein has a tendency to slowly oligomerize (oligomers are soluble structures containing a plurality of monomers) prior to proceeding into the inert fibrillar state. This oligomeric state has recently been implicated as a neurotoxic agent and, therefore, as the toxic species involved in AD (Haass, C., and Selkoe, D. J., Nature Reviews Mol. Cell. Biol. 8: 101-112 (2007)). The prevalent method for producing these toxic structures at physiological conditions involve incubating peptide solutions at 20-100 μM and 4° C. in cell culture medium (F-12) or in buffered salt solutions for several days (Lambert, M. P., et al., Proc. Natl. Acad. Sci. USA. 95: 6448-6453 (1998); Stine, W. B., et al., J. Biol. Chem. 278: 11612-11622 (2003)). Because nucleation and elongation rates are strongly dependent on peptide concentration (Lomakin, A., et al., Proc. Natl. Acad. Sci. USA 93: 1125-1129 (1996)), any increase in the concentration of peptide above 100 μM will be detrimental to the stability of the oligomer preparation. In the classical view of amyloid fibril assembly, the nuclei triggering polymerization and the oligomeric structures are even believed to be the same species. Oligomer preparations therefore have a very limited and unpredictable (aggregation nucleation is a spontaneous event) lifespan once they are formed. In dilute solutions (20 μM to 25 μM) at 4° C. oligomer preparations of Aβ(42) are typically stable only for 24 h, and those of Aβ(40) for maybe a week. In less dilute solutions, >100 μM, the insolubility of the Aβ protein decreases dramatically. The fibrillation process is thus a serious drawback when, as in screening assays for medicaments, stable proteins are required at relatively high concentration.

The aim of the present invention is to overcome these problems by providing engineered Aβ peptides that form stabile oligomers.

There are no previous reports of stabilized Aβ hairpin structures and no reports of Aβ peptides containing only the A21C/A30C disulphide without additional complicating cysteines. US 2006/0018918 discloses Aβ isomers based on a consideration of the Aβ primary structure alone with multiple cysteine replacement of all Ser and Ala in general with the intent of stabilizing non-native conformations of Aβ to be used as vaccines. The A21C and A30C mutations are obtained together with three or four additional cysteine mutants at position Ala2, Ser8, Ser26, and Ala42. Oxidation of these Aβ isomers produces a mixture of 15 possible isoforms with different intramolecular disulphide bonds where only three of the 15 possible isoforms will contain an A21C/A30C disulphide bond, but always in combination with additional disulphide bonds.

Previous Aβ peptide disulfide mutants reported in the literature are L17C/L34C, L17C/M35C, and L17CN36C (Shivaprasad, S. and Wetzel, R., Biochemistry 43: 153-15317 (2004)). These mutations are all non-conservative replacements. Furthermore, these mutants were made specifically to investigate the proximity of Leu17 to Leu34, Met35, and Val36 in the fibril structure. Shivaprasad and Wetzel present data that demonstrate that these three mutants undergo fibrillogenesis with lag times that are nearly identical for the reduced (with the mutated residues as cysteines) and oxidized (with the mutated residues as cystines) mutants. Other disulphide mutants, which are also non-conservative replacements, have been published by the same authors, namely V18C/L34C, F19C/A30C, F19C/I32C, and F19C/L34C (Wetzel, R., et al., Biochemistry 46: 1-10 (2007)). These mutants were found to behave similarly to the L17C/L34C, L17C/M35C, and L17CN36C mutants. Hence, all previously published disulphide mutants of the Aβ protein have been demonstrated to readily aggregate into fibrils of at least similar stability to the fibrils obtained from wild-type peptide. These oxidized derivatives of the L17C/L34C, L17C/M35C, L17CN36C, V18C/L34C, F19C/A30C, F19C/I32C, and F19C/L34C mutants all fibrillate because they are incompatible with the hairpin structure presented in Hoyer et al. (Hoyer, W. et al., Proc. Natl. Acad. Sci. USA. 105: 5099-5104 (2008)) whereas they are compatible with current models of Aβ-peptide fibril structures where the two β-strands pack against each other (see e.g. Petkova, A. T., et al., Biochemistry 45: 498-512).

Aβ oligomer preparations are described in WO 2007/005358, WO 2007/005359, WO 2007/142320 and WO 2004/067561. These described oligomer preparations have been obtained by using intermolecular crosslinkers (WO 2007/005358), non-physiological pH (pH 9 in WO 2007/005359) and/or additives (40% glycerol or TFE were claimed to stabilize oligomers at 37° C. in WO 2007/005359; GM1 ganglioside in WO 2007/142320; and SDS in WO 2004/067561).

SUMMARY OF THE INVENTION

The present invention provides covalently constrained monomeric and oligomeric Aβ A21C/A30C peptides that are resistant towards fibrillogenesis. The peptides according to the invention retain most of its wild-type like properties as probed by size exclusion chromatography (SEC), far-UV CD (indicative of coil structure), and NMR (also coil-like). Since the fibrillation step is blocked, the Aβ peptides according to the invention populate several low molecular-weight oligomers with coil-structure (eluting from SEC as up to approximately 42 kDa proteins), as well as high molecular-weight oligomers with β-structure (eluting from SEC as approximately 75-85 kDa and 170 kDa proteins) upon concentration. Furthermore, wild-type-like protofibrillar structures with dimensions of 6 nm width and typically 30 nm in length are obtained by heating concentrated protein solutions. The high molecular-weight oligomers with β-structure are recognized by the A11 polyclonal antibody.

BRIEF DESCRIPTION OF THE INVENTION

The present invention provides monomeric and oligomeric Aβ peptides with an unprecedented resistance towards fibrillogenesis.

In order to prevent aggregation side-reaction from depleting the pool of concentrated monomeric and oligomeric Aβ peptide, the present inventors have designed covalently constrained Aβ peptides. The Aβ peptides according to the invention comprise amino acids replacements at positions 21 and 30 in the wild-type Aβ(40) (SEQ ID NO: 1) or Aβ(42) (SEQ ID NO: 2) peptides with cysteines, resulting in intra-molecularly disulphide bonded Aβ(40) A21C/A30C (SEQ ID NO: 3) and Aβ(42) A21C/A30C (SEQ ID NO: 4) peptides (FIG. 1A). These amino acids replacements effectively block the conformational switch that triggers amyloidosis, one hypothesis of this mechanism is schematically depicted in FIG. 1B, and allows for the population of several oligomeric states, including the high molecular-weight oligomers with β-structure that are considered to be the toxic species. The Aβ peptides according to the invention form potentially toxic oligomeric states that are similar to those obtained for the wild-type Aβ peptide, having a far-UV circular dichroism (CD) spectrum identical to wild-type oligomers, and they also bind the A11 antibody, and form protofibrils with wild-type-like morphology. The non-oligomeric coil-like state of the Aβ peptides according to the invention also remain wild-type-like as probed by size SEC, far-UV CD spectroscopy, and $^{15}N$ heteronuclear single quantum coherence (HSQC) nuclear magnetic resonance (NMR) spectroscopy.

Because of the constraining disulphide bond present in the peptides according to the invention, other methods to stabilize oligomers are not needed, including (i) non-physiological (elevated) pH to increase repulsion of the peptides, (ii) using additives including 2,2,2-trifluoroethanol (TFE), sodium dodecyl sulphate (SDS), glycerol, or cell membrane glycolipids in the form of GM1 gangliosides, to induce oligomeric structure, (iii) adding anions to screen charges thus increasing solubility, and (iv) using an intermolecular cross-link that covalently stabilizes the oligomers once they are prepared by one or several of alternatives (i)-(iii). The Aβ peptides according to the invention are in fact the first examples of Aβ peptides forming stable oligomers under physiological conditions, this being obtained by arresting the fibrillation step. Furthermore, long incubation times and unpredictable outcomes of oligomeric preparations are avoided, as the Aβ peptides according to the invention can be purified and rapidly concentrated into the oligomeric states.

In one aspect, the present invention provides peptides comprising the amino acid sequence LVFFC (SEQ ID NO: 13) corresponding to amino acids 17 to 21 of SEQ ID NO: 4, and the amino acid sequence CIIGLMV (SEQ ID NO: 14) corresponding to amino acids 30 to 36 of SEQ ID NO: 4. The peptide according to the invention further comprises a disulphide bond between the amino acids corresponding to Cys21 and Cys30 in SEQ ID NO: 4. In one preferred aspect of the invention, said peptide is obtained by linking the peptide comprising the amino acid sequence LVFFC SEQ ID NO: 13) to the peptide comprising the amino acid sequence CIIGLMV (SEQ ID NO: 14 by an inter-molecular disulphide bond. In a more preferred aspect of the invention, said two peptides are constituents of a single peptide chain with an intra-molecular disulphide bond between Cys21 and Cys30. Furthermore, the amino acid sequence LVFFC (SEQ ID NO: 13) is fused to the amino acid sequence CIIGLMV (SEQ ID NO: 14) by a peptide comprising 4 to 20 amino acids, such as 6 to 16, preferably 7 to 12, or even more preferably 8 to 10 amino acids, such as 9 amino acids. The present invention further provides variants of said peptides wherein one or more, such as one, two, three, four, five, or preferably one or two, amino acids have been replaced by conservative substitution, one or more, such as one, two, three, four, five, or preferably one or two, amino acids have been deleted, or one or more, such as one, two, three, four, five, or preferably one or two, amino acids have been inserted.

Preferably, the fusion peptide comprises the amino acid sequence EDVGSNKG (SEQ ID NO: 15) corresponding to amino acids 22 to 29 of SEQ ID NO: 4. Accordingly, the peptides according to the invention preferably comprise the amino acid sequence LVFFCEDVGSNKGCIIGLMV (SEQ ID NO: 16) corresponding to amino acids 17 to 36 of SEQ ID NO: 4, and variants of said peptides wherein one or more, such as one, two, three, four, five, or preferably one or two, amino acids have been replaced by conservative substitution, one or more, such as one, two, three, four, five, or preferably one or two, amino acids have been deleted, or one or more, such as one, two, three, four, five, or preferably one or two, amino acids have been inserted.

Even more preferably, the peptides according to the invention comprise the amino acid sequence 1 to 40 of SEQ ID NO: 4, the full amino acid sequence SEQ ID NO: 4, and variants of said peptides wherein one or more, such as one, two, three, four, five, or preferably one or two, amino acids have been replaced by conservative substitution, one or more, such as one, two, three, four, five, or preferably one or two, amino acids have been deleted, or one or more, such as one, two, three, four, five, or preferably one or two, amino acids have been inserted.

The peptides according to the invention can further comprise a glycine substitution at the position corresponding to amino acid 22 (SEQ ID NO: 5), or a glutamine substitution at the position corresponding to amino acid 22 (SEQ ID NO: 6), or a lysine substitution at the position corresponding to amino acid 22 (SEQ ID NO: 8). The peptides according to the invention can also comprise an asparagine substitution at the position corresponding to amino acid 23 (SEQ ID NO: 7). The peptides according to the invention can also comprise a methionine sulphoxide residue at the position corresponding to amino acid 35 in SEQ ID NO: 4.

Furthermore, the peptides according to the invention can comprise (a) one or two terminal amino acids being maleimidated; (b) one or two terminal amino acids being cysteinylated; (c), the carboxy terminal end of the peptide has been amidated, i.e. the free COOH at the carboxy terminal has been transformed into $CONH_2$; and/or the amino terminal end of the peptide has been acetylated, i.e. the free $NH_2$ group at the amino terminal has been transformed into the amide $CH_3CONH$— (AcNH—). The peptides according to the invention can be prepared by chemical synthesis or be prepared by recombinant DNA technology.

By conservative substitution is meant substitution of one amino acids with an amino acid having similar properties with regard to polarity and hydrophobicity. Examples of groups of amino acids having such similar properties are provided in Table 1. Conservative substitution can also include substitution with a non-standard amino acid. Non-standard amino acids include, but are not limited to, the examples within brackets in Table 1, where PL is pyrrolysine, DA is dehydroalanine, NL is norleucin, SC is selenocysteine, HC is homocysteine, CL is citrulline, and OR is ornithine.

TABLE 1

| Hydrophobic (apolar) | A V L I P F W M [PL DA NL] | | |
|---|---|---|---|
| Polar (uncharged) | G S T C Y N Q [SC HC CL] | | |
| Polar (charged) | D E K R H [OR] | Positively charged | H K R [OR] |
| | | Negatively charged | E D |

Preferably, conservative substitutions and amino acid insertions according to the invention do not allow for insertion of further cysteines in addition to the cysteines corresponding to Cys21 and Cys30 in SEQ ID NO: 4.

Preferably, conservative substitutions and amino acid deletions according to the invention do not allow for replacement or deletion of the cysteines corresponding to Cys21 and Cys30 in SEQ ID NO: 4.

Most preferably, the Aβ peptides according to the invention always comprise exactly two cysteines, i.e. the cysteines corresponding to Cys21 and Cys30 in SEQ ID NO: 4.

The peptides according to the invention are substantially resistant towards fibrillogenesis. By being resistant to fibrillogenesis is meant that said peptides do not form fibrils under near-physiological conditions where wild type Aβ peptide fibrillate, as demonstrated by several of the examples presented herein. In one aspect the present invention provides soluble oligomers consisting of peptides according to the invention.

In another aspect the present invention provides an antibody specifically reacting with a peptide according to the invention. This antibody can be a monoclonal antibody. In another aspect the present invention provides an antibody fragment specifically reacting with a peptide according to the invention. The antibody fragment can be a Fab fragment, a (Fab)$_2$ fragment, a single chain Fab fragment, a single chain Fv fragment, or a single chain Fv dimer. In yet another aspect the present invention provides a protein binder specifically reacting with a peptide according to the invention. Said protein binders include, but are not limited to, derivatives of the anticalin, Affibody, FNfi10, neocarzinostatin, ankyrin repeat protein, PDH finger, CDR3 grafted green fluorescent protein, and *E. coli* periplasmic binding protein scaffolds.

In another aspect the present invention provides methods for the identification of a compound suitable for the treatment of a disease caused by, or related to, the deposition of protein fibrils or amyloids, said method comprising the use of a peptide according to the invention. The disease can be an amyloidosis, such as an amyloid neuropathy or cerebral amyloid angiopathy, a prion disease such as Creurtfeldt-Jakob disease, bovine spongiform encephalopathy, or scrapie, Parkinson's disease, or Alzheimer's disease. Preferably the disease is Alzheimer's disease. The method for the identification of a compound suitable for the treatment of a disease caused or related to the deposition of protein fibrils or amyloids, can comprise:
  a) providing a test compound,
  b) contacting said test compound with a peptide according to the invention,
  c) determining if the test compound binds to the peptide and/or inhibits the formation of peptide oligomers,
  d) identifying said compound as suitable for the treatment of a disease caused or related to the deposition of protein fibrils or amyloids disease.

The disease can be an amyloidosis, such as an amyloid neuropathy or cerebral amyloid angiopathy, a prion disease such as Creurtfeldt-Jakob disease, bovine spongiform encephalopathy, or scrapie, Parkinson's disease, or Alzheimer's disease. Preferably the disease is Alzheimer's disease.

In another aspect the present invention provides methods for identifying and/or selecting binding proteins, said method comprising the use of a peptide according to the invention. The binding molecule can be an antibody fragment, such as a Fab fragment, a (Fab)$_2$ fragment, a single chain Fab fragment, a single chain Fv fragment, or a single chain Fv dimer. The binding molecule can also be engineered non-natural receptor derivatives, such as derivatives of the anticalin, Affibody, FNfn10, neocarzinostatin, ankyrin repeat protein. PDH finger, CDR3 grafted green fluorescent protein, and *E. coli* periplasmic binding protein scaffolds.

In yet another aspect the present invention provides use of a peptide according to the invention in the preparation of pharmaceutical compositions intended for immunization for prophylactic or therapeutic treatment of a disease caused by, or related to, the deposition of protein fibrils or amyloids, optionally in combination with an adjuvant. The disease can be an amyloidosis, such as an amyloid neuropathy or cerebral amyloid angiopathy, a prion disease such as Creuztfeldt-Jakob disease, bovine spongiform encephalopathy, or scrapie, Parkinson's disease, or Alzheimer's disease. Preferably the disease is Alzheimer's disease.

In yet another aspect the present invention provides pharmaceutical preparations comprising a therapeutically effective amount of a peptide according to the invention, optionally in combination with an adjuvant. In yet another aspect the present invention provides vaccines for immunization of mammals, including humans, against a disease caused by, or related to, the deposition of protein fibrils or amyloids, comprising a peptide according to the invention, optionally in combination with an adjuvant. The disease can be an amyloidosis, such as an amyloid neuropathy or cerebral amyloid angiopathy, a prion disease such as Creurtfeldt-Jakob disease, bovine spongiform encephalopathy, or scrapie, Parkinson's disease, or Alzheimer's disease. Preferably the disease is Alzheimer's disease.

In yet another aspect the present invention provides vaccines for immunization of mammals, including humans, against a disease caused by, or related to, the deposition of protein fibrils or amyloids, comprising a therapeutically effective amount of an antibody according to the invention. The disease can be an amyloidosis, such as an amyloid neuropathy or cerebral amyloid angiopathy, a prion disease such as Creurtfeldt-Jakob disease, bovine spongiform encephalopathy, or scrapie, Parkinson's disease, or Alzheimer's disease. Preferably the disease is Alzheimer's disease.

In yet another aspect the present invention provides methods for prophylactic or therapeutic treatment of a mammal, including a human being, suffering from a disease caused by, or related to, the deposition of protein fibrils or amyloids or facing the risk of developing a disease caused by, or related to, the deposition of protein fibrils or amyloids, whereby a therapeutically effective amount of a peptide according to the invention is administered to said mammal. The disease can be an amyloidosis, such as an amyloid neuropathy or cerebral amyloid angiopathy, a prion disease such as Creurtfeldt-Jakob disease, bovine spongiform encephalopathy, or scrapie, Parkinson's disease, or Alzheimer's disease. Preferably the disease is Alzheimer's disease.

In yet another aspect the present invention provides methods for prophylactic or therapeutic treatment of a mammal, including a human being, suffering from a disease caused by, or related to, the deposition of protein fibrils or amyloids or facing the risk of developing a disease caused by, or related to, the deposition of protein fibrils or amyloids, whereby a therapeutically effective amount of an antibody according to the invention is administered to said mammal.

DESCRIPTION OF THE FIGURES

FIG. 3E represents the baselines without peptide. Fibrillation was monitored by TFT binding (10 μM) and the assays were carried out at 37° C. with shaking in phosphate buffer at pH 7.2.

DETAILED DESCRIPTION OF THE INVENTION

The invention provides covalently constrained Aβ peptides having A21C/A30C disulphide replacements that are resistant towards fibrillogenesis, and their use in the screening for therapeutic agents against toxic oligomeric species involved in Alzheimer's and other protein misfolding diseases. The peptides according to the invention can also be used directly as immunogens to raise an immune response against toxic forms of the Aβ peptide. The invention is an example of the use of rational peptide engineering to modify peptide properties to suit new needs; the need here being the desire to arrest Aβ peptide fibrillogenesis at the toxic oligomeric level so that these species can be isolated and utilized. The examples presented below demonstrate that the peptides according to the invention share many properties of the wild-type Aβ peptide except the high tendency of wild-type Aβ peptide to fibrillate.

Herein, the term oligomer is used as a collective term for soluble aggregates containing a plurality of Aβ-peptide monomers. These monomers are peptide fragments derived from the APP (Swiss-Prot entry P05067), and are commonly comprised of 39 to 43 amino acids. The full length sequence is described in Kang, J., et al., Nature 325: 773-776 (1987). The invention provides stabilized peptides corresponding to all of the 39 to 43 residue long derivatives of the APP including the two most frequently encountered derivatives, Aβ(40) and Aβ(42), for which the sequences are:

Human Aβ(40):
DAEFRHDSGYEVHHQKLVFFAEDVGSNK-GAIIGLMVGGVV (SEQ ID NO: 1)
Human Aβ(42):
DAEFRHDSGYEVHHQKLVFFAEDVGSNK-GAIIGLMVGGVVIA (SEQ ID NO: 2)

Accordingly, one preferred aspect of the invention provides peptides comprising the following sequences:

```
Human Aβ(40) A21C/A30C:
                                      (SEQ ID NO: 3)
DAEFRHDSGYEVHHQKLVFFCEDVGSNKGCIIGLMVGGVV Human Aβ(42) A21C/A30C:
                                      (SEQ ID NO: 4)
DAEFRHDSGYEVHHQKLVFFCEDVGSNKGCIIGLMVGGVVIA
```

Single-letter symbols and three-letter symbols are exchangeable used to denote the amino acids. These symbols, which are well known to man skilled in the art, have the following meaning: A=Ala=alanine, C=Cys=cysteine, D=Asp=aspartic acid, E=Glu=glutamic acid, F=Phe=phenylalanine, G=Gly=glycine, H=His=histidine, I=Ile=isoleucine, K=Lys=lysine, L=Leu=leucine, M=Met=methionine, N=Asn=asparagine, P=Pro=proline, Q=Gln=glutamine, R=Arg=arginine, S=Ser=serine, T=Thr=threonine, V=Val=valine, W=Trp=tryptophan, and Y=Tyr=tyrosine.

Figure 1A:
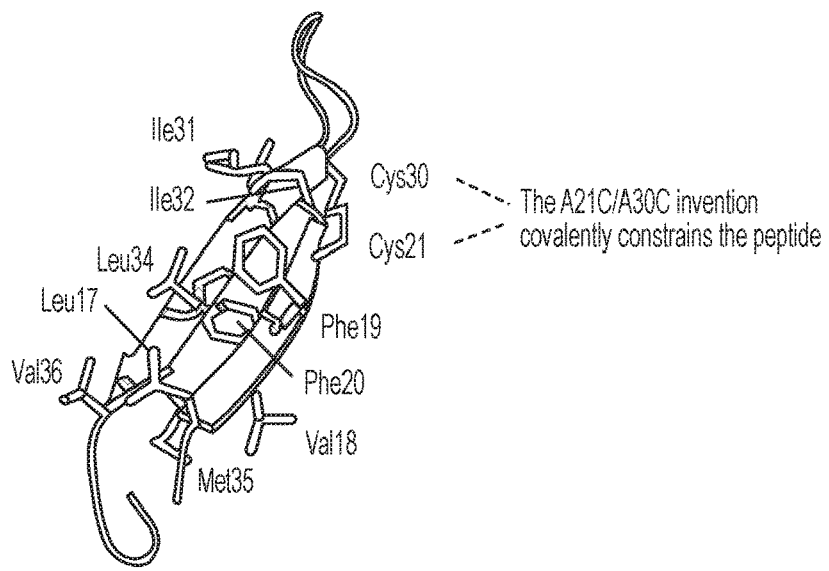
FIG. 1A represents a drawing of the hairpin structure of the Aβ-peptide (Protein Data Bank accession no. 2OTK) with the introduced cysteines at positions 21 and 30 and the disulphide bond linking these two positions (SEQ ID NO: 4). Leu17, Phe19, Cys21, Cys30, Ile32, Leu34, and Val36 comprising the upwards facing side of the structure; and Val18, Phe20, Ile31, and Met35 comprising the downward facing side of the structure, this side also contains Gly33.
Figure 1B:
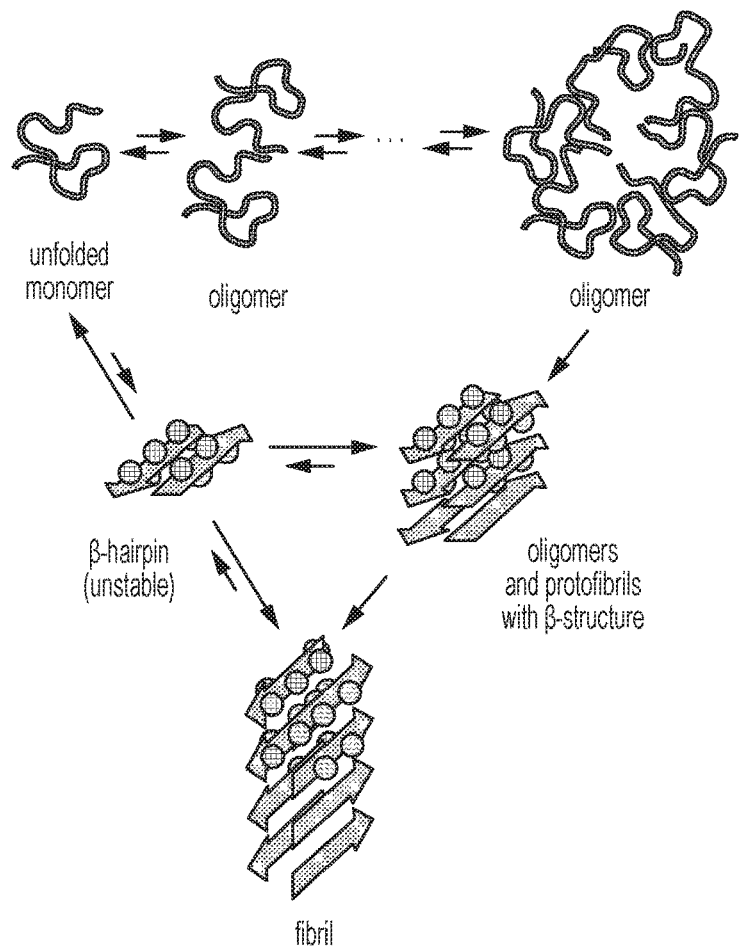
FIG. 1B represents a schematic depiction of a hypothetical aggregation scheme. In this hypothesis, the amfiphilic Aβ peptide spontaneously self-associates into micellar-like oligomeric structures of low molecular weight that are weakly stabilized by hydrophobic forces (coil-like oligomers). The β-hairpin is only transiently occupied, but is stable in the high molecular-weight oligomeric structures that form by hydrophobic stacking. The color coding of the hairpin is the same as in FIG. 1A. Fibrillogenesis occurs as a result of a conformational switch whereby the hydrogen bonds and hydrophobic van der Waals bonds in the β-structured oligomer are broken and reformed in a much more stable fibril structure, wherein the two β-strands colored in orange are now facing each other in the fibril core. This conformational step is arrested by the disulphide bond connecting positions 21 and 30, thus allowing for the other states to become populated.

The peptides according to the invention was specifically designed in order to prevent fibrillation of the Aβ peptides derived from the APP. Design of the peptides according to the invention (FIG. 1A) is based on the recently determined NMR structure (Protein Data Bank accession no. 2OTK) of the Aβ peptide (Hoyer, W., et al., Proc. Natl. Acad. Sci. USA. 105: 5099-5104 (2008)). The constraining disulfide bond present in the peptides of the invention connecting residues 21 and 30 stabilizes this β-hairpin structure once it is formed, and further inhibits the conformational switch that triggers amyloidosis, (one hypothesis of such a mechanism is schematically depicted in FIG. 1B. In consequence, the Aβ peptides according to the invention are very resistant towards fibrillogenesis even at high concentrations unless the disulphide bond is reduced (disrupted) to form thiols (RSH) with e.g. dithiothreitol (DTT), β-mercaptoethanol, or TCEP, under physiological conditions, under which the intramolecular covalent link between Cys21 and Cys30 is stable. Further oxidation of the sulphides to sulphenic (RSOH), sulphinic (RSO$_2$H), and sulphonic (RSO$_3$H) acid with e.g. reactive oxygen species (such as H$_2$O$_2$) or similar harsh treatments under non-physiological conditions, is likely to trigger fibrillogenesis of this peptide.

Positions 21 and 30 of the Aβ peptide (as defined in e.g. SEQ ID NO: 2) are the only two residues that can be covalently linked by a disulphide bond without disrupting said β-hairpin structure. Two geometrical criteria must be fulfilled for such a successful incorporation of a stabilizing disulphide bond, namely (1) that the $C_\alpha$-$C_\alpha$ distance between the positions that are to be linked are within 4.4-6.8 Å, and (ii) that the $C_\beta$-$C_\beta$ distance between the same two residues are within 3.45-4.50 Å (Clarke, J., and Fersht, A., Biochemistry 32: 4322-4329 (1993)). In addition, similar peptide engineering is likely to be applicable on all Aβ peptide derivatives that are capable of forming said hairpin structure either as the transiently occupied monomeric species, or as the stable oligomeric species. Accordingly, the invention is not limited to A21C/A30C Aβ peptides corresponding to the 39 to 43 residue long AO peptides with wild-type sequences, but also includes A21C/A30C Aβ peptides corresponding to naturally occurring Aβ-peptide mutants that lead to an increased incidence of familial AD. These mutations can be found in any of the 39-43 long Aβ-peptide derivatives of the APP. The invention thus includes, but is not limited to A21C/A30C Aβ peptides carrying, the E22G arctic mutation (SEQ ID NO: 5), the E22Q Dutch mutation (SEQ ID NO: 6), the D23N Iowa mutation (SEQ ID NO: 7), and the Italian E22K mutation (SEQ ID NO: 8), and other familial mutations that are likely to appear. Furthermore, the hairpin structure in said sequences containing a methionine sulphoxide or sulphone at position 35 can be stabilized by the invention. This methionine is believed by many to be essential for toxicity (see e.g. Butterfield, D. A., and Kanski, J., Peptides 23: 1299-1309 (2002)).

Other A21C/A30C Aβ peptides comprising one or more conservative mutations or otherwise made conservative substitutions, alterations, insertions or truncations (e.g. the 9-42 truncated derivative; SEQ ID NO: 9) of the above mentioned sequences, including non-standard amino acids and end terminal modifications, such as cysteinylation, maleimidation, acetylation, and amidation, are also part of the invention, and are fibrillization-resistant. Amino acids outside of the β-hairpin structure, i.e. residues 1 to 16 and 37 to 40 of SEQ ID NO: 3, and 1 to 16 and 37 to 42 of SEQ ID NO: 4, are more resilient to substitution and, therefore, even non-conservative replacements in these regions are tolerated without seriously affecting the function of the invention. Other modified A21C/A30C Aβ peptides that are part of the invention include, but is not limited to, peptides wherein one or more consecutive stretches of Aβ-peptide sequence have been inverted, such as the 1-8 N-terminal inverted derivative (SEQ ID NO: 10). The Aβ peptides according to the invention can be produced by chemical synthesis followed by separation of oxidized peptides (sulphides) from reduced peptides (thiols) by reverse-phase high-performance liquid chromatography (HPLC) as previously described for other disulfide derivatives of this peptide (Shivaprasad, S. and Wetzel, R., Biochemistry 43: 153-15317 (2004)). Chemical synthesis is the most common way to produce the Aβ peptides. Since these AO peptides are usually lyophilized, it may first be necessary to pretreat the peptides with 100% 1,1,1,3,3,3-hexafluoro-2-propanol (HFIP) to remove pre-existing aggregates prior to characterization as discussed previously (Stine, W. B. et al. J. Biol. Chem. 278: 11612-11622 (2003)).

Other A21C/A30C Aβ peptides comprising one or more conservative mutations or otherwise made conservative substitutions, alterations, insertions or truncations (e.g. the 9-42 truncated derivative; SEQ ID NO:9) of the above mentioned sequences, including non-standard amino acids and end terminal modifications, such as cysteinylation, maleimidation, acetylation, and amidation, are also part of the invention, and are fibrillization-resistant. Amino acids outside of the β-hairpin structure, i.e. residues 1 to 16 and 37 to 40 of SEQ ID NO:3, and 1 to 16 and 37 to 42 of SEQ ID NO:4, are more resilient to substitution and, therefore, even non-conservative replacements in these regions are tolerated without seriously affecting the function of the invention. Other modified A21C/A30C Aβ peptides that are part of the invention include, but is not limited to, peptides wherein one or more consecutive stretches of Aβ-peptide sequence have been inverted, such as the 1-8 N-terminal inverted derivative (SEQ ID NO:10). The Aβ peptides according to the invention can be produced by chemical synthesis followed by separation of oxidized peptides (sulphides) from reduced peptides (thiols) by reverse-phase high-performance liquid chromatography (HPLC) as previously described for other disulfide derivatives of this peptide (Shivaprasad, S. and Wetzel, R., Biochemistry 43: 153-15317 (2004)). Chemical synthesis is the most common way to produce the Aβ peptides. Since these Aβ peptides are usually lyophilized, it may first be necessary to pretreat the peptides with 100% 1,1,1,3,3,3-hexafluoro-2-propanol (HFIP) to remove pre-existing aggregates prior to characterization as discussed previously (Stine, W. B. et al. J. Biol. Chem. 278: 11612-11622 (2003)).

Heterologous expression of the Aβ peptides according to the invention in *Escherichia coli* is an alternative to chemical synthesis, but requires for the peptides to be expressed as fusion proteins to aid its solubility (see e.g. Lee, E. K., et al., Prot. Expr. Purif. 40:183-189 (2005)). A method of choice for cost-efficient production of Aβ(40) and Aβ(42) is to co-express these peptides with an affinity binding protein (Grönwall, C., et al., J. Biotechnol. 128: 162-183 (2007)) in *E. coli*. In brief, the peptides are expressed concomitantly with the binding protein, thus forming a soluble complex that protects the Aβ peptide against aggregation and proteolysis. The binding protein contains a hexa-histidine tag to aid in the purification of the complex using immobilized metal affinity chromatography (IMAC). Once purified, the complex can be broken using GdmCl, and the released Aβ peptide can be separated from the affinity binding protein again using IMAC under denaturing conditions. The GdmCl can then be dialyzed away or removed using SEC. This co-expression protocol does not involve lyophilization, and enables for direct selection of the peptides during expression. As a result from expression in *E. coli*, all the peptides used in the data presented below contain an extra N-terminal methionine. We here denote this position as −1, so that the amino acid sequence in the Aβ peptides retain their original numbering. The extra methionine does not limit or affect the property of the peptides, and similar results are obtained with wild-type Aβ and A21C/A30C Aβ peptides if synthesized and purified as previously described (Shivaprasad, S. and Wetzel, R., Biochemistry 43: 153-15317 (2004)).

Aggregation assays of Aβ(40) A21C/A30C were carried out under near-physiological conditions (50 mM $K^+$ phosphate buffer, 50 mM NaCl, pH 7.2) at various concentrations at 37° C. with shaking. These experiments demonstrate that this peptide is very resistant towards fibrillogenesis, and that the reduced (in the presence of 5 mM TCEP) fully fibrillated species have TFT binding properties comparable to wild-type peptide (Example 1). Two features are evident when the same experiment is carried out at higher concentrations of peptide (Example 2): First, there is a rapid initial increase in TFT fluorescence at concentrations exceeding 100 μM that subsequently declines to similar levels in all samples; Second, as the concentration of peptide increases; there is also an increase in lag times preceding fibrillation in the reduced samples. These two observations are features of the oligomeric tendencies of this peptide: The rapid increase in fluorescence is a result of the initial formation of protofibrillar-like species that subsequently dissociate as a new equilibrium is established, and the increased lag-times are likely to be a result of the disulphide bond being more or less inaccessible in the coil-like oligomers that exist at high concentration.

Apart from being resistant towards fibrillogenesis, the Aβ(40) A21C/A30C peptide resembles the wild-type peptide. CD and NMR spectra of the low molecular-weight fraction (eluting at approximately 8 kDa) obtained from SEC demonstrate that said peptide forms coil-like structures that are very similar to wild type peptide (Example 3). At higher concentrations several oligomeric species containing a plurality of monomers elute from the SEC runs. These frequently elute within the range of >8 to <42 kDa (Example 4), and they all have coil-like structures with CD spectra identical to the peptide obtained in the low molecular-weight fraction. These coil-like oligomers are denoted low molecular-weight oligomers. However, the peptide is also capable of forming larger oligomers with β structures. These structures elute from the SEC columns as proteins of sizes of approximately 75-85 kDa and 170 kDa (Example 5). We herein denote these β structured oligomers as high molecular-weight oligomers. In aggregation assays, these high molecular-weight oligomers are resistant towards fibrillogenesis. Even the presence of 10 mM TCEP could not nucleate polymerization of these oligomers at 30 µM peptide concentration (Example 5). Some of these high molecular-weight oligomers also bind the A11 antibody (Example 6), which is a polyclonal antibody specifically raised against Aβ peptide oligomers and is suggested to be generic for disease-related oligomeric species (Kayed, R. et al. *Science* 300: 486-489 (2003)).

Low molecular-weight oligomers of the peptides of the invention at high concentration can be made to form protofibril-like structures rapidly by the application of heat (60° C.) (Example 7). This step has not been optimized, and other elevated temperatures (approximately >20° C.) will have the same effect, although a temperature below 80° C. is desirable to prevent irreversible covalent modifications of the peptide from occurring (including deamidation of Asn27 and Gln15, as well as oxidation of the Cys21-Cys30 disulphide bond and Met35). According to TEM, these protofibrils have an average dimension of approximately 6.7 nm in width, and lengths in the order of approximately 36 nm (although the lengths vary) (Example 8). The transition is accompanied by the formation of β structure, for which the CD spectrum is indistinguishable from the high molecular-weight oligomers above. These structures also bind TFT. In aggregation assays, this structural transition therefore results in a rapid initial increase in fluorescence, which is followed by a gradual decrease when the protofibrils dissociate as a new equilibrium is established. This observation is consistent with the view that Aβ-peptide protofibrils are in equilibrium with monomeric species but at the same time being fibril precursors (Walsh, D. M., et al., *J. Biol. Chem.* 274: 25945-25952 (1999)).

The longer peptides according to the invention, i.e. the Aβ(42) derivatives (Example 9) are also protected from fibrillization, and the oligomers thus obtained during SEC of Aβ(42) A21C/A30C have a similar size distribution as the Aβ(40) A21C/A30C oligomers (Example 10). The A11 epitope is present in the largest of the high molecular-weight oligomers with β structure that elute from the SEC column (Example 10). This A11-binding epitope is very stable once formed and only decreases with 0.1% per day when incubated at 37° C. over a two-month period (Example 11).

The peptides according to the invention, when used for the production of covalently stabilized oligomers, provides advantages over previous methods in that these peptide's resistance towards fibrillogenesis enables such oligomers to be prepared under physiological conditions. These oligomers can then be studied at higher concentrations and/or for longer times than previously possible, thus aiding considerably in drug screening assays and immunization trials. High molecular-weight oligomers of the Aβ peptides according to the invention can be produced (e.g. as in example 5), concentrated, and then used in methods for the identification of compounds potentially suitable for the treatment of AD. Such a compound should bind to already formed toxic oligomers and dissolve them, and/or prevent their formation. There are several biophysical techniques that can be used to monitor the disruption of preexisting oligomeric structures or their non-existence including CD, NMR, isothermal titration calorimetry, or enzyme-linked immunosorbent assays using an antibody or binding protein specific for the oligomeric or monomeric structures. Even the fluorophores 1-anilino-8-naphthalene sulfonate and TFT, which both fluoresces when bound to the oligomers, can be used in such an assay as the fluorescence is quenched upon oligomer dissociation. A person skilled in the art will realize that there are several other possibilities. In another embodiment of the invention, the covalently stabilized monomers or oligomers may be used for the preparation of antigen formulations as immunogens for the generation of antibodies or other protein binders. Both active and passive immunization against the hairpin structure here shown to be present in the potentially toxic oligomeric forms of AD may come into question.

In yet another aspect the present invention provides non-human transgenic animals expressing a nucleotide sequence encoding an amyloid precursor protein (APP) comprising the A21C/A30C mutations. Preferably, the APP is a mutated human APP comprising the A21C/A30C mutations, most preferably the APP is the protein SEQ ID NO: 11. Preferably, the nucleotide sequence is a mutated human APP gene comprising the A21C/A30C mutations. The non-human transgenic animal is preferably selected from the phylum Chordata (and Hemichordata), such as a vertebrate animal (which include cyclostomes, bony fish, sharks and rays, amphibians, reptiles, mammals, and birds). Preferably, the non-human transgenic animal is a mammal, such as a mouse, rat, pig, rabbit, or guinea pig. Most preferably the non-human transgenic mammal is a mouse.

In another embodiment of the invention, non-human transgenic animals can be used as model systems for AD pathogenesis by overexpressing only an Aβ peptide according to the invention comprising the A21C/A30C replacements. As no proteolytic processing of APP is required to generate the toxic Aβ peptide in such a model organism, non-human transgenic animals may not only be selected from within the chordates (and hem ichordates), but may also include invertebrates which lack endogenous APP comprising the Aβ peptide (e.g. selected from any of the phyla Annelida, Arthropoda, Cnidaria, Echinodermata, Mollusca, Nematoda, Nematomorpha, Platyhelminthes, and Porifera). Invertebrate models of AD pathogenesis have the advantage of short life spans, low costs, small sizes, and highly characterized genetics. Examples of such invertebrate model systems include *Drosophila melanogaster* (Crowther, D. C. et al. (2005) Neuroscience 132: 123-135) and *Caenorhabditis elegans* (Link, C. D. (1995) Proc. Natl. Acad. Sci. USA 92: 9368-9372). Accordingly, in yet another aspect the present invention provides non-human transgenic animals expressing a nucleotide sequence encoding an Aβ peptide according to the invention comprising the A21C/A30C replacements. Preferably, the heterologously expressed Aβ peptide in such an invertebrate model system is the peptide corresponding to SEQ ID NO: 3, SEQ ID NO: 4, SEQ ID NO: 5, SEQ ID NO: 6, SEQ ID NO: 7, SEQ ID NO: 8 SEQ ID NO: 9 and/or SEQ ID NO: 10.

In yet another aspect the present invention provides a nucleotide sequence encoding an APP comprising the A21C/A30C mutations. Preferably the APP is a mutated human APP comprising the A21C/A30C mutations, most preferably the APP is the protein SEQ ID NO: 11. Preferably the nucleotide sequence is a mutated human APP gene comprising the A21C/A30C mutations.

Another aspect of the present invention is an expression system comprising a nucleotide sequence encoding APP comprising the A21C/A30C mutations. Yet another aspect of the present invention is a polypeptide which is an APP comprising the A21C/A30C mutations, preferably a mutated human APP comprising the A21C/A30C mutations, most preferably the polypeptide SEQ ID NO: 11.

The amino acid position 21 in the human Aβ peptide corresponds to the amino acid position 692 in human APP, and amino acid position 30 in the human Aβ peptide corresponds to the amino acid position 701 in human APP. The sequence of human APP can be found in Swiss-Prot entry P05067 (SEQ ID NO: 12). Consequently, by an APP comprising the A21C/A30C mutations is meant an APP wherein i) the amino acid alanine in position 692, as defined by the sequence of the human APP (SEQ ID NO: 12) or the corresponding position in a homologous or heterologous APP, is replaced with a cysteine, and ii) the amino acid alanine in position 701, as defined by the sequence of the human APP (SEQ ID NO: 12) or the corresponding position in a homologous or heterologous APP, is replaced with a cysteine.

By a homologous or heterologous APP is meant an APP derived from an animal, such as a vertebrate, as well as a synthetic, mutated, and/or non naturally occurring APP, which has a sequence identity of at least 80%, such as at least 90%, or at least 95% as compared to human APP (SEQ ID NO: 12). The percent identity between two amino acid sequences is determined as follows. First, an amino acid sequence is compared to, for example, SEQ ID NO: 12 using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information web site at ncbi.nlm.nih.gov. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences. The percent identity is determined by dividing the number of matches by the length of the sequence set forth in an identified sequence followed by multiplying the resulting value by 100. For example, if a sequence is compared to the sequence set forth in SEQ ID NO: 12 (the length of the sequence set forth in SEQ ID NO: 12 is 770) and the number of matches is 693, then the sequence has a percent identity of 90 (i.e., 693÷770×100=90) to the sequence set forth in SEQ ID NO: 12.

Production of Transgenic Animals

Methods for generating transgenic animals of the present invention are well known in the art (see, generally, Gene Targeting: A Practical Approach, Joyner, ed., Oxford University Press, Inc. (2000)). In one embodiment, generation of the transgenic mouse may optionally involve disruption of the murine APP genes and introduction of one or more copies of the gene encoding a mutated human APP into the murine genome, preferably at the same location as the endogenous murine APP gene.

The transgenic non-human animals of the invention are preferably produced by introducing transgenes into the germline of the animal. Embryonic target cells at various developmental stages can be used to introduce transgenes. Different methods are used depending on the stage of development of the embryonic target cell. The specific line(s) of any animal used to practice this invention are selected for general good health, good embryo yields, good pronuclear visibility in the embryo, and good reproductive fitness. When transgenic mice are to be produced, strains such as C57BL/6 or C57BL/6×DBA/2 F1, or FVB lines are often used (obtained commercially from Charles River Labs, Boston, Mass., The Jackson Laboratory, Bar Harbor, Me., or Taconic Labs.).

Introduction of the transgene into the embryo can be accomplished by any means known in the art such as, for example, microinjection, electroporation, or lipofection. For example, the transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. One common method is to incubate the embryos in vitro for about 1-7 days, depending on the species, and then reimplant them into the surrogate host. Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Retroviral infection can also be used to introduce transgenes into non-human animals. The developing non-human embryo can be cultured in vitro to the blastocyst stage. During this time, the blastomeres can be targets for retroviral infection (Jaenich, R. (1976) *Proc. Natl. Acad. Sci. USA* 73:1260-1264). Efficient infection of the blastomeres is obtained by enzymatic treatment to remove the zona pellucida (Manipulating the Mouse Embryo, Hogan eds., Cold Spring Harbor Laboratory Press, Cold Spring Harbor, 1986). The viral vector system used to introduce the transgene is typically a replication-defective retrovirus carrying the transgene (Jahner et al. (1985) *Proc. Natl. Acad. Sci. USA* 82:6927-6931; Van der Putten et al. (1985) *Proc. Natl. Acad. Sci. USA* 82:6148-6152). Transfection is easily and efficiently obtained by culturing the blastomeres on a monolayer of virus-producing cells (Van der Putten, supra; Stewart et al. (1987) *EMBO J.* 6:383-388). Alternatively, infection can be performed at a later stage. Virus or virus-producing cells can be injected into the blastocoele (Jahner et al. (1982) *Nature* 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem (ES) cell. Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal.

In one embodiment of the invention, an endogenous APP gene in a nonhuman host is functionally disrupted by homologous integration of a heterologous APP gene comprising the A21C/A30C mutations, such that the heterologous APP gene substantially replaces the endogenous APP gene, and preferably completely replaces the coding sequences of the endogenous APP gene. Preferably, the heterologous APP gene is linked, as a consequence of homologous integration, to regulatory sequences (e.g., an enhancer/promoter) of the endogenous APP gene, respectively, so that the heterologous gene is expressed under the transcriptional control of regulatory elements from the endogenous APP gene locus. Nonhuman hosts which are homozygous for such replacement alleles may be produced according to methods described herein. Such homozygous nonhuman hosts generally will express a heterologous APP but do not express the endogenous APP protein. Usually, the expression pattern of the heterologous humanized APP gene will substantially mimic the expression pattern of the endogenous APP gene, in the naturally-occurring (non-transgenic) nonhuman host.

For example, a transgenic mouse can be generated that has APP gene sequences comprising the A21C/A30C mutations in place of endogenous murine APP gene sequences and which are transcriptionally controlled by endogenous murine regulatory sequences. The APP gene sequences comprising the A21C/A30C mutations generally will be expressed similarly to the murine APP in naturally occurring non-transgenic mice.

Generally, a replacement-type targeting construct is employed for homologous gene replacement. Double-crossover homologous recombination between endogenous APP gene sequences of the targeting construct result in targeted integration of the heterologous APP gene segments. Usually, the homology targeting regions of the transgene comprise sequences which flank the endogenous APP gene segments, so that homologous recombination results in concomitant deletion of the endogenous APP, and homologous integration of the heterologous APP gene segments. Substantially an entire endogenous APP gene may be replaced with a heterologous APP by a single targeting event or by multiple targeting events (e.g., sequential replacement of individual exons). One or more selectable markers, usually in the form of positive or negative selection expression cassettes, may be positioned in the targeting construct. It is usually preferred that selectable markers are located in intron regions of the heterologous replacement region.

Transgenic animals comprising transgene APP gene sequences comprising the A21C/A30C mutations can be crossed with other transgenic animals, generating transgenic animals comprising multiple transgenes. A manner of preparation is to generate a series of mammals, each containing one of the desired knockout constructs or transgenes. Such mammals are bred together through a series of crosses, backcrosses and selections, to ultimately generate a single mammal containing all desired knockout constructs and/or transgenes, where the mammal is otherwise congenic (genetically identical) to the wild type except for the presence of the knockout(s) constructs and/or transgene(s). Typically, crossing and backcrossing is accomplished by mating siblings or a parental strain with an offspring, depending on the goal of each particular step in the breeding process. In certain cases, it may be necessary to generate a large number of offspring in order to generate a single offspring that contains each of the knockout constructs and/or transgenes in the proper chromosomal location. In addition, it may be necessary to cross or backcross over several generations to ultimately obtain the desired genotype.

EXAMPLES

Example 1. Fibrillation Assay of Wild-Type Aβ(40) and Aβ(40) A21C/A30C

All concentration determinations were carried out spectrophotometrically using an extinction coefficient of 1424 $cm^{-1} M^{-1}$ for the difference in absorption at 280 nm and 300 nm. The buffered solution used in all examples was 50 mM $K^+$ phosphate, 50 mM NaCl, pH 7.2, unless otherwise stated. This buffer was also the storage buffer for the Aβ peptides. All peptide samples were prepared fresh, kept at 4° C., and used within 3-4 days.

Fibrillation assays were carried out by monitoring the enhanced fluorescence of the dye TFT upon binding to the fibrils (Levine, H., *Methods Enzymol.* 309: 274-284 (1999)). Fluorescence was recorded in 96-well plates (Nunc) using a FLUOstar Optima reader (BMG) equipped with 440 nm excitation and 480 nm emission filters. The peptide samples were kept at 30 µM and were supplemented with 10 µM TFT. In addition, 5 mM TCEP was added to one reference sample of the invention to assay the effect of the formed disulphide bond. TCEP is a more stable reductant than the more commonly used DTT at basic pH. It reduces the disulphide bonds to thiols, thus disrupting the constraining covalent bond of the invention. Prior to measurements, plates were sealed with polyolefin tape (Nunc) to prevent evaporation. The assay was carried out at 37° C., and data points were recorded every 6 min with 2 min of orbital shaking (width 5 mm) preceding each measurement.

Figure 2:
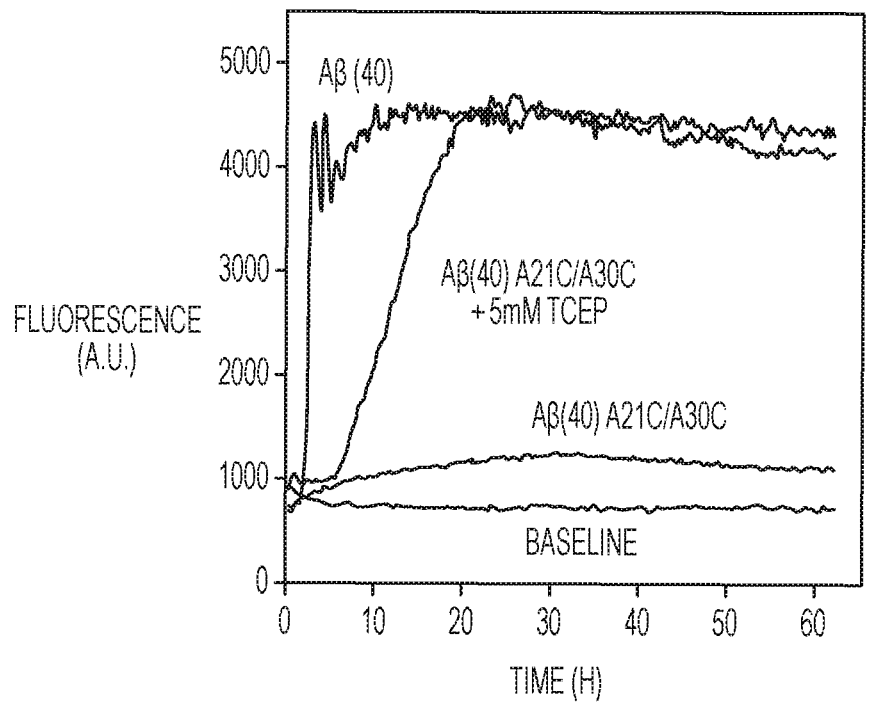
FIG. 2 represents fibrillation assays of the Aβ(40) peptide with and without the A21C/A30C replacements, as well as the Aβ(40) A21C/A30C peptide with a broken disulphide bond (in 5 mM tris(2-carboxyethyl) phosphine (TCEP)). Fibrillation was monitored by Thioflavin T (TFT) binding (10 μM) and the assays were carried out at 37° C. with shaking in phosphate buffer at pH 7.2.
Figure 3A:
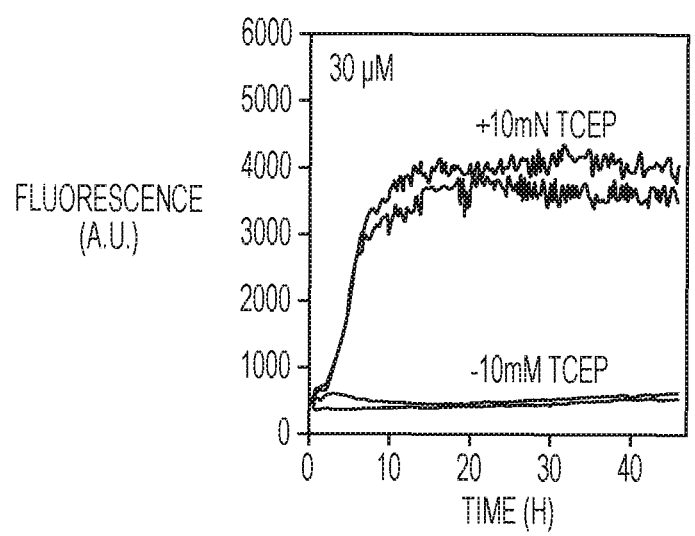
FIGS. 3A-3E represent fibrillation assays of the Aβ(40) A21C/A30C peptide with formed and broken (by 10 mM TCEP) disulphide bonds at 30 μM (FIG. 3A), 50 μM (FIG. 3B), 150 μM (FIG. 3C) and 250 μM (FIG. 3D) peptide.
Figure 3B:
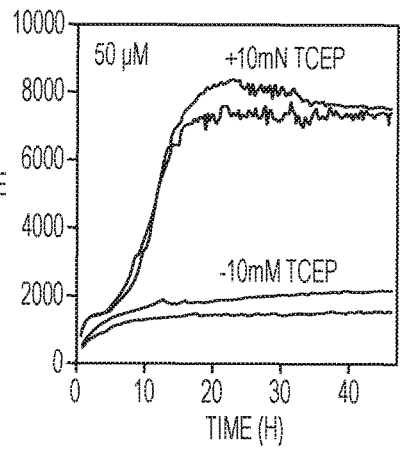
Figure 3C:
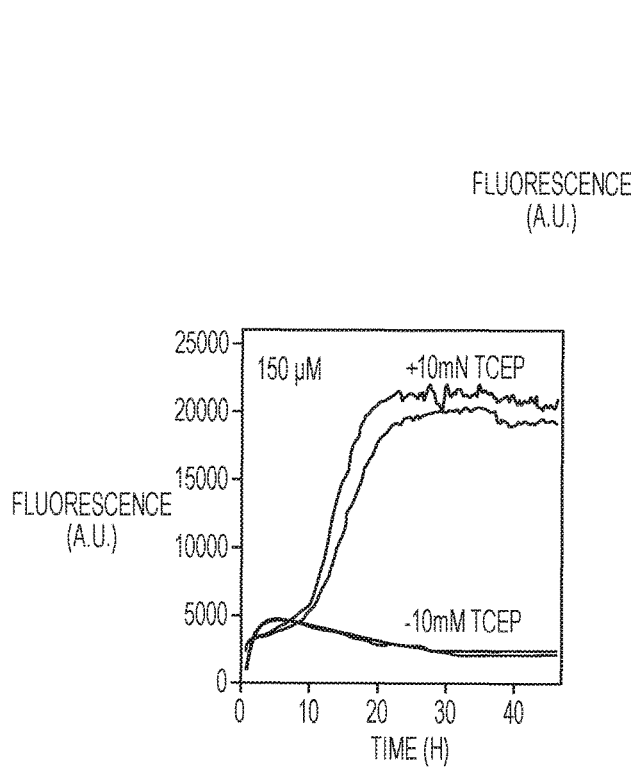
Figure 3D:
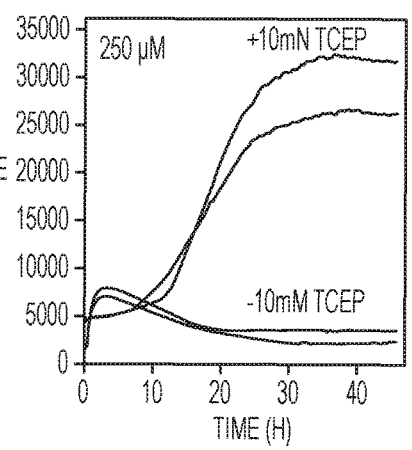
Figure 3E:
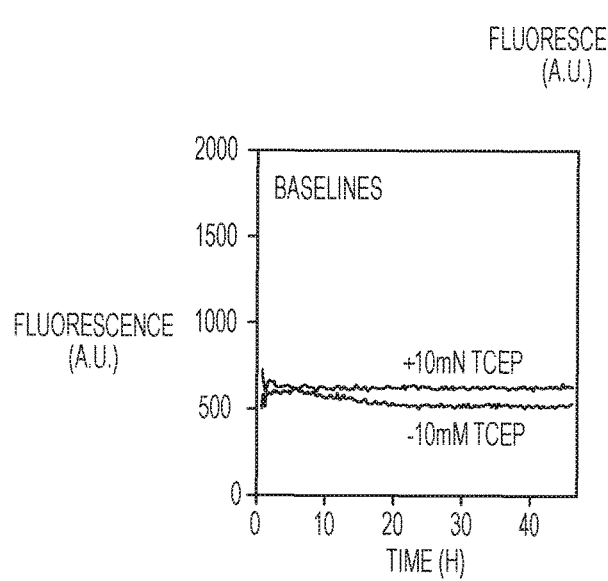

The result of this aggregation assay is presented in FIG. 2. Nucleation and fibrillation occurs rapidly in the wild-type sample. For the A21C/A30C peptide reduced with TCEP, the lag time is approximately 5 h longer, but the TFT fluorescence of the fully fibrillated end state is identical to the wild-type fibril. For the oxidized A21C/A30C peptide, on the other hand, there is no fibrillation occurring.

Example 2. Fibrillation Assays of Aβ(40) A21C/A30C at Increasing Concentrations

The fibrillation assay was carried out as in example 1, except that the concentration of peptide was also assayed at 50, 150, and 250 μM, and the TCEP concentration was increased to 10 mM TCEP in the reference samples. Also, data points were recorded every 15 min with 5 min of orbital shaking (width 5 mm) preceding each measurement. Dual samples were analyzed at each concentration, and the result is presented in FIG. 3.

The result is similar to the result obtained in Example 1. However, there is a rapid increase in fluorescence for the samples with an intact disulphide bond at the 150 and 250 μM concentrations, which then decline to similar levels with much slower rates. As demonstrated in Examples 7 and 8 below, the coil-like oligomers can be made to form protofibrillar-like structures when subjected to elevated temperatures, and these do bind TFT weakly thus giving rise to enhanced fluorescence. As time progresses, a new equilibrium is reached in these samples. Observations made by Walsh et al. for the wild-type Aβ peptide are applicable to the data in FIG. 3 (Walsh, D. M., et al., J. Biol. Chem. 274: 25945-25952 (1999)). They show data that suggest that the protofibrils are fibril precursors, and that the competing rate constants for protofibril dissociation and fibril formation are of similar magnitude. But the conformational switch triggering fibrillation in wild-type Aβ Aβ peptide is inhibited in the Aβ A21C/A30C peptide, which is why no fibrils can be detected in these highly concentrated samples unless the disulphide bond is broken. The slower increase in fluorescence in the 50 μM sample is likely due to the fact that the protofibrils are not nucleated at this lower concentration, but that the structural transition from coil-to β-structure nevertheless occurs as a result of the higher temperature and/or agitation of the sample. It has indeed been shown previously that that binding of TFT is dependent on the presence of β-sheet structure (DeLellis, R. A., et al., J. Histochem. Cytochem. 16: 663-665 (1968)).

Another feature of the increased peptide concentration is the increase in lag times preceding nucleation for the Aβ A21C/A30C peptide with broken disulphide bonds. It is probable that this is the combined result of (i) that the coil-like oligomers present in these samples (see Example 4) have more or less protected disulphide bonds, and (ii) that more peptide requires more time to be reduced with TCEP.

Example 3. Wild-Type-Like Structure of Aβ(40) A21C/A30C

SEC was carried out on a Superdex 75 10/300 column (GE Healthcare) equilibrated with 50 mM K$^+$ phosphate, 50 mM NaCl, pH 7.2. The flow rate was 0.8 ml min$^{-1}$, and the column was operated by an ÄKTA Explorer unit (GE Healthcare). All column runs were carried out at room temperature (21° C.). The column was calibrated with a low molecular-weight gel filtration calibration kit (Amersham Biosciences) under similar conditions. Typically, 500 μl of peptide was injected into this column during each run.

At low concentrations of peptide, e.g. 25 μM, the Aβ(40) A21C/A30C peptide typically elutes as an approximately 8-10 kDa protein. Even though the Aβ peptide is approximately a 4.5 kDa protein, we do not interpret this as this peptide is eluting as a dimer because of the potentially extended structures of unfolded coil-like proteins compared to the well-folded proteins used in the calibration kit (ribonucelase A, chymotrypsinogen A, ovalbumin, and albumin). In the experiment shown in FIG. 4A, 25 μM of Aβ(40) A21C/A30C peptide was injected into the column, thus generating a single symmetrical peak corresponding to approximately an 8 kDa protein. SEC of Aβ(40) wild-type peptide yields identical results on this column (not shown), and the apparent size of 8-10 kDa is on the order of what has been demonstrated previously (e.g. in Walsh, D. M., et al., J. Biol. Chem. 272: 22364-22372 (1997)).

A far-UV CD spectrum was collected on a Jasco J-810 spectropolarimeter (Jasco Corporation) at 20° C. using a scan rate of 50 nm min$^{-1}$. In the experiment presented in FIG. 4B, 20 μM of Aβ(40) A21C/A30C peptide was scanned between 190-260 nm in a 1.0 mm cuvette. The spectrum exhibits a minimum around 200 nm that is typical of coil-like structures, and is very similar to CD spectra of non-aggregated Aβ(40) and Aβ(42) wild-type peptide (not shown; for examples see e.g. Walsh, D. M., et al., J. Biol. Chem. 274: 25945-25952 (1999)).

SDS PAGE was carried out using the Criterion Gel system (Bio-Rad) and precast 16.5% Tris-Tricine gels (Bio-Rad) at a constant voltage of 120V. The running medium was 100 mM Tris-HCl, 100 mM Tricine, and 0.1% SDS (pH 8.3). In FIG. 4C, a 300 μM sample of Aβ(40) A21C/A30C peptide was mixed in a 1:1 ratio with loading buffer (50 mM Tris-HCl, 1% SDS, 20% glycerol, and 0.23% bromphenol blue), and one sample was also made 2.5 mM TCEP. The sample containing TCEP was incubated at 95° C. for 5 min, whereas the sample lacking TCEP was incubated at room temperature (21° C.) for approximately 20 min. A volume of 6 μl was then loaded onto the gel together with peptide markers. The gel was run, fixed in 50% methanol and 10% acetic acid (for approximately 1 h), and stained with Coomassie Brilliant Blue for 16 h (0.1% Coomassie, 2.5% 2-propanol, 10% acetic acid). After destaining (5% methanol, 7% acetic acid) the gels were analyzed. As shown in FIG. 4C, both samples migrate close to the 6.2 kDa peptide marker band, thus demonstrating that only an intramolecular disulphide bond has formed in the Aβ(40) A21C/A30C peptide.

$^{15}$N-HSQC NMR spectroscopy was measured on a Varian Inova 800 MHz spectrometer on $^{15}$N-labelled Aβ(40) A21C/A30C peptide at 50 μM and 1.9 mM concentrations of low molecular-weight oligomers (with coil structure), and on a 50 μM and 450 μM sample of high molecular-weight oligomers (with β-structure). The spectrum in FIG. 4D on 50 μM peptide is indicative of an unstructured coil-like peptide, and is similar to published spectra of the wild-type Aβ peptide (Hou, L., et al., J. Am. Chem. Soc. 126: 1992-2005 (2003)). Both 50 μM spectra are nearly identical (not shown). The 1.9 mM spectrum of low molecular-weight oligomers and that of 450 μM high molecular-weight oligomers were also identical with only a few visible peaks (not shown), indicating that these structures are too large for solution NMR. The visible peaks in the latter two spectra probably stem from the mobile parts of these oligomers.

Taken together, this example thus demonstrates that the peptides according to the invention have structural properties very similar to wild type Aβ peptide despite the presence of an intramolecular disulphide bond. That the disulphide bond is formed is demonstrated in Examples 1 and 2.

Example 4. SEC Analysis of the Oligomeric Tendencies of the Aβ(40) A21C/A30C

SEC on the Superdex 75 10/300 column was carried out as in Example 3. The larger Superdex 75 16/60 column (GE Healthcare) was operated similarly to the smaller 10/300 column, except that it was run at 1.0 ml min$^{-1}$ and that 1 ml was loaded.

Figure 4A:
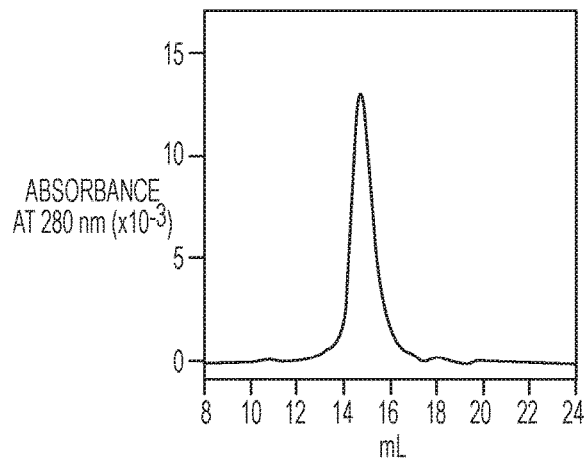
FIG. 4A represents the SEC elution profile of the Aβ(40) A21C/A30C peptide at low concentrations (approximately 25 μM), whereby said peptide elutes as approximately an 8 kDa protein.
Figure 4B:
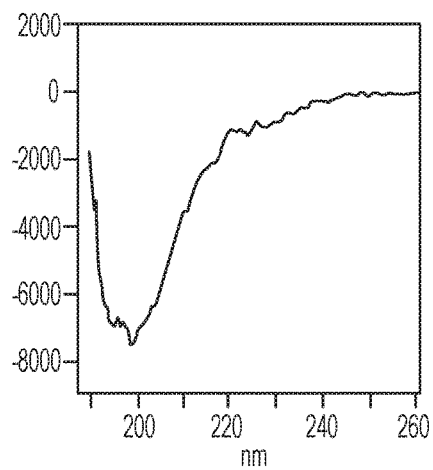
FIG. 4B represents a far-UV CD spectrum of the Aβ(40) A21C/A30C peptide as a coil-like protein. This spectrum is virtually identical for all coil-like preparations of said peptide.
Figure 5:
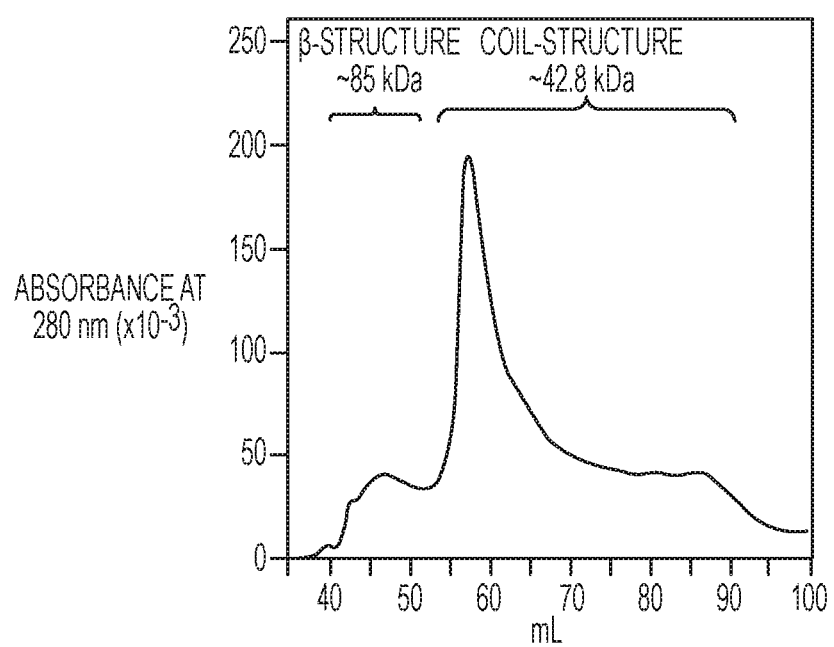
FIG. 5 represents an SEC elution profile of a concentrated solution (at approximately 1.8 mM) of Aβ(40) A21C/A30C peptide that was denatured in 6M guanidinium chloride (GdmCl) prior to SEC. According to far-UV CD spectroscopy, the high molecular-weight fractions all have β structure, and the low molecular-weight fractions all have coil structure.

FIG. 5 shows one experiment to assay the distribution of oligomers under higher concentration of peptide than that used in FIG. 4A. The Aβ(40) A21C/A30C peptide was denatured in 6 M guanidinium chloride (GdmCl), 50 mM K$^+$ phosphate, 50 mM NaCl (pH 7.2), which destroys pre-existing oligomers. GdmCl is a compound routinely used as a protein denaturant. A solution of approximately 1.8 mM denatured peptide was injected into the Superdex 75 16/60 column. On the column, the peptide molecules become separated from the GdmCl and are free to oligomerize. Under these conditions, the Aβ(40) A21C/A30C peptide elutes as a distribution of soluble structures. The dominating peak elutes at a position which, according to the protein calibration kit (same as in Example 3), corresponds to approximately a 42 kDa globular protein. Again, we believe that SEC does not give an accurate determination of Aβ peptide sizes, and these numbers can only be used in a relative sense. CD spectroscopy demonstrated that the oligomers in this peak has coil-like structure (not shown; the far-UV CD spectrum is virtually identical to FIG. 4B). The distribution of these coil structures ranges down to species eluting as approximately 8 kDa proteins. The larger oligomeric species that elutes as an 85 kDa species has a far-UV CD spectrum consistent with β structure (not shown; the far-UV CD spectrum of this fraction is virtually identical to FIG. 7B).

Figure 6A:
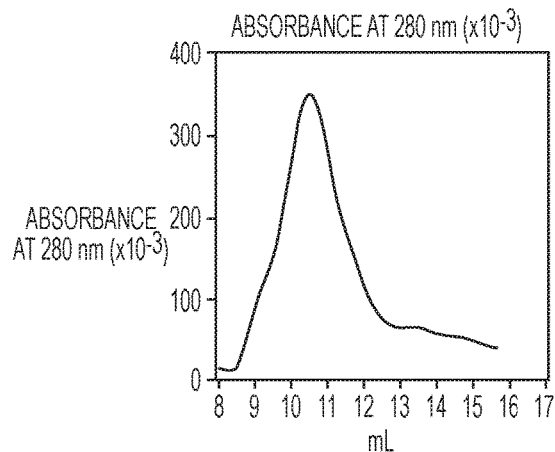
FIG. 6A represents an SEC elution profile of a concentrated solution (at approximately 1.5-1.8 mM) of Aβ(40) A21C/A30C peptide that was denatured in 6M GdmCl prior to SEC.
Figure 6B:
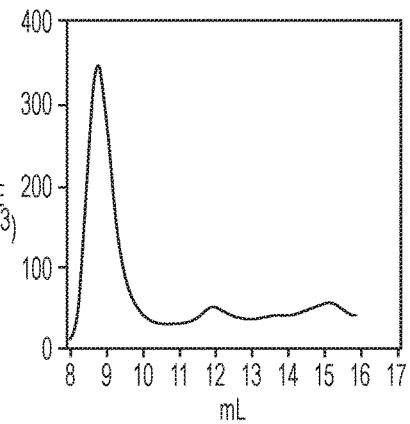
In FIG. 6B the same solution was pre-treated with β-mercaptoethanol prior to SEC on the same column and in the same buffer supplemented with 5 mM TCEP to keep the cysteines reduced. The peptide elutes in the void under these conditions (as >100 kDa proteins).

In a related experiment shown in FIG. 6A, a similar concentration of denatured Aβ(40) A21C/A30C peptide was loaded onto a Superdex 10/300 column. The elution profile exhibits the same features as in FIG. 5, although with lower resolution. As a comparison, SEC on the same denatured sample first pre-treated with approximately 35 mM β-mercaptoethanol for 10 min at room temperature (21° C.) and gelfiltrated in the same buffer supplemented with 5 mM TCEP gives almost exclusively high molecular-weight oligomers or protofibrils eluting in the void volume (>100 kDa) (FIG. 6B). The CD spectrum of this fraction is dominated by β structure (not shown; the far-UV CD spectrum of this fraction is virtually identical to FIG. 7B).

Figure 6C:
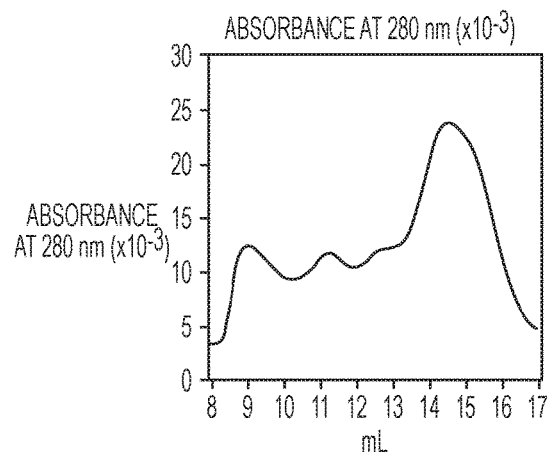
FIG. 6C represents the SEC elution profile of the top fraction in FIG. 6A after 4 days at 4° C. and a concentration of 200 μM.
Figure 6D:
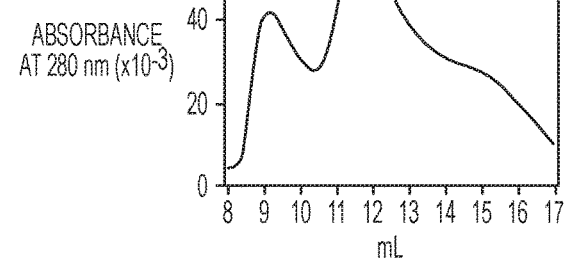
FIG. 6D represents the SEC elution profile of the peak centered around 10.8 ml in FIG. 6A concentrated to approximately 1 mM.

The top fraction of the oligomeric peak around 10.8 mL in FIG. 6A, having a concentration of 200 μM, was incubated for 4 days at 4° C. and then gelfiltrated again. The elution profile of this sample in FIG. 6C shows that a new equilibrium has been established during this time, and that the species eluting as an 8 kDa protein now dominates. In contrast, pooling all fractions of the oligomeric peak in FIG. 6A after 4 days at 4° C. and concentrating this solution to approximately 1.0 mM and reanalyzing it on the same column gives rise to a profile where again larger oligomeric structures dominate.

Figure 4C:
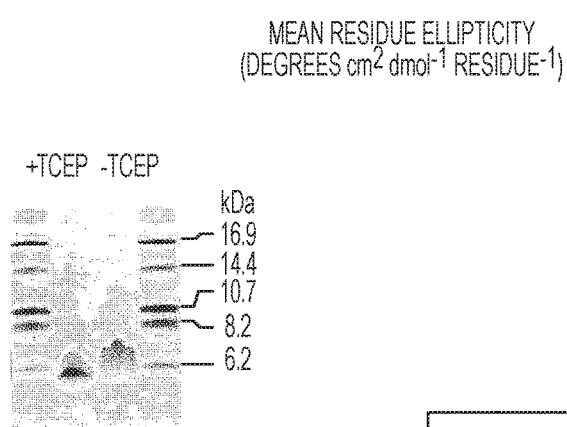
FIG. 4C represents an SDS polyacrylamide gel electrophoresis (PAGE) analysis of the Aβ(40) A21C/A30C peptide with formed (−TCEP) and broken (+TCEP) disulphide bonds.
Figure 4D:
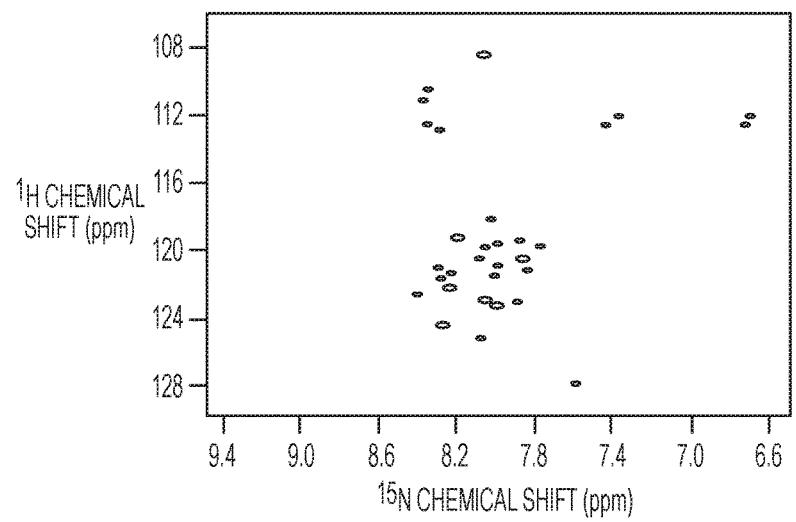
FIG. 4D represents a $^{15}$N-HSQC NMR spectrum of 50 μM Aβ(40) A21C/A30C peptide.

Taken together, the SEC experiments demonstrate that by blocking the fibrillation step the Aβ A21C/A30C peptide readily form several types of oligomers containing different pluralities of monomers. The low molecular-weight fractions that elute as >8 kDa to <42 kDa proteins all have similar coil-like far-UV CD spectra (an example of such a spectrum is shown in FIG. 4B). The high molecular-weight fractions elute as >75 kDa proteins and they all have similar far-UV CD spectra consistent with β-structure (an example of such a spectrum is shown in FIG. 7B).

Example 5. Preparation and Characterization of High Molecular-Weight Oligomers of Aβ(40) A21C/A30C SEC was carried out as in Example 3, with a Sephacryl S-300 26/60 column (GE Healthcare) where 1 ml was injected into the column, which was run at 1.3 ml min$^{-1}$. The column had been calibrated previously as in Example 3. An approximately 1.7 mM Aβ(40) A21C/A30C peptide solution denatured in 6 M GdmCl, 50 mM K$^+$ phosphate, 50 mM NaCl, pH 7.2, was injected into this larger column and the elution profile is presented in FIG. 7A. Under these conditions, the high molecular-weight fractions elute as β-structured oligomers at approximately 170 kDa and 80 kDa, whereas the coil-oligomers elute as smaller proteins.

A far-UV CD spectrum of Aβ(40) A21C/A30C peptide was collected as in Example 3. In the experiment presented in FIG. 7B, 250 μM of Aβ(40) A21C/A30C peptide that eluted from a SEC run at volumes corresponding to 75-85 kDa was scanned between 185-260 nm in a 0.1 mm cuvette. The spectrum exhibits a minimum around 210 nm and positive ellipticity around 190 nm that is typical of β-like structures of the Aβ(40) and Aβ(42) peptides as they oligomerize and aggregate (e.g. Walsh, D. M., et al., *J. Biol. Chem.* 274: 25945-25952 (1999)). Both the 170 kDa and 80 kDa species in FIG. 7A exhibited far-UV CD spectra nearly identical to the spectrum in FIG. 7B.

Figure 8:
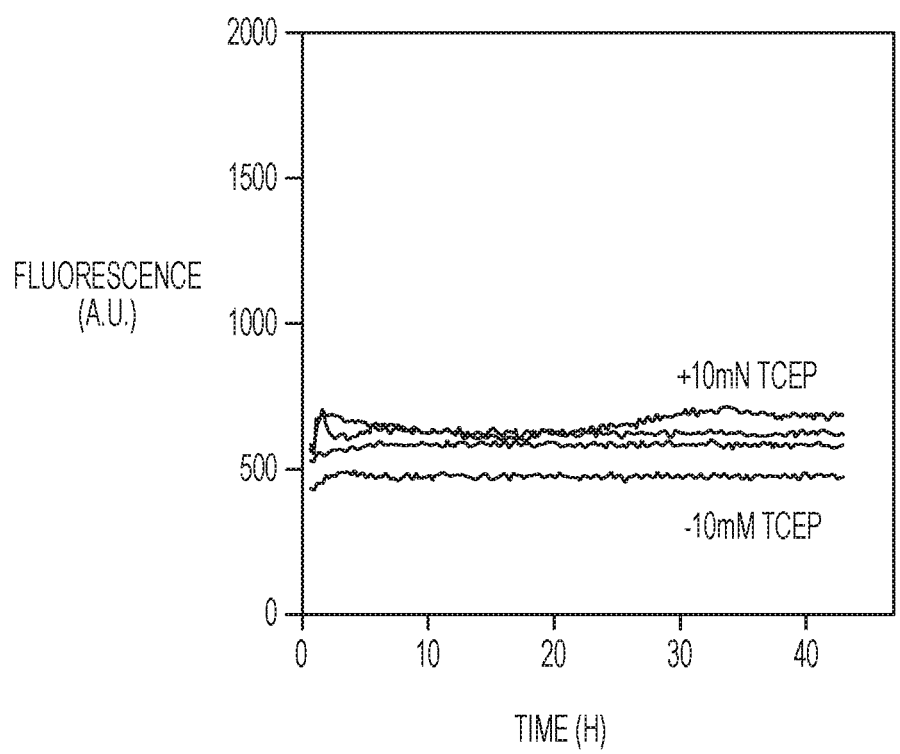
FIG. 8 represents a fibrillation assay of the Aβ(40) A21C/A30C peptide as β-structured oligomer with and without (in 10 mM TCEP) the constraining disulphide bond. Fibrillation was monitored by TFT binding (10 μM) and the assay was carried out at 37° C. with shaking in phosphate buffer at pH 7.2.

Fibrillation assays of 30 μM (monomeric peptide concentration) high molecular-weight oligomers of the Aβ(40) A21C/A30C peptide was carried out as in Example 2, with dual samples with and without 10 mM TCEP (FIG. 8). During the course of the experiment, there were no fibrils appearing in any of the samples. The baseline is the same as in FIG. 3E.

Example 6. High Molecular-Weight Oligomers of Aβ(40) A21C/A30C Bind the A11 Polyclonal Antibody Purified rabbit immunoglobulins recognizing a synthetic molecular mimic of soluble Aβ-peptide oligomers (the A11 polyclonal antibody) has been shown to also recognize similar oligomers in other proteins involved in protein-misfolding diseases (Kayed, R., et al., *Science* 300: 486-489 (2003)). Since the oligomeric structures are believed to be the toxic species in these diseases this suggests a common mechanism of pathogenesis and, hence, probably also that similar toxic structures are involved (Haass, C., and Selkoe, D. J., *Nature Reviews Mol. Cell. Biol.* 8: 101-112 (2007); Glabe, C. G., *Trends Biochem. Sci.* 29: 542-547 (2004)).

Figure 9:
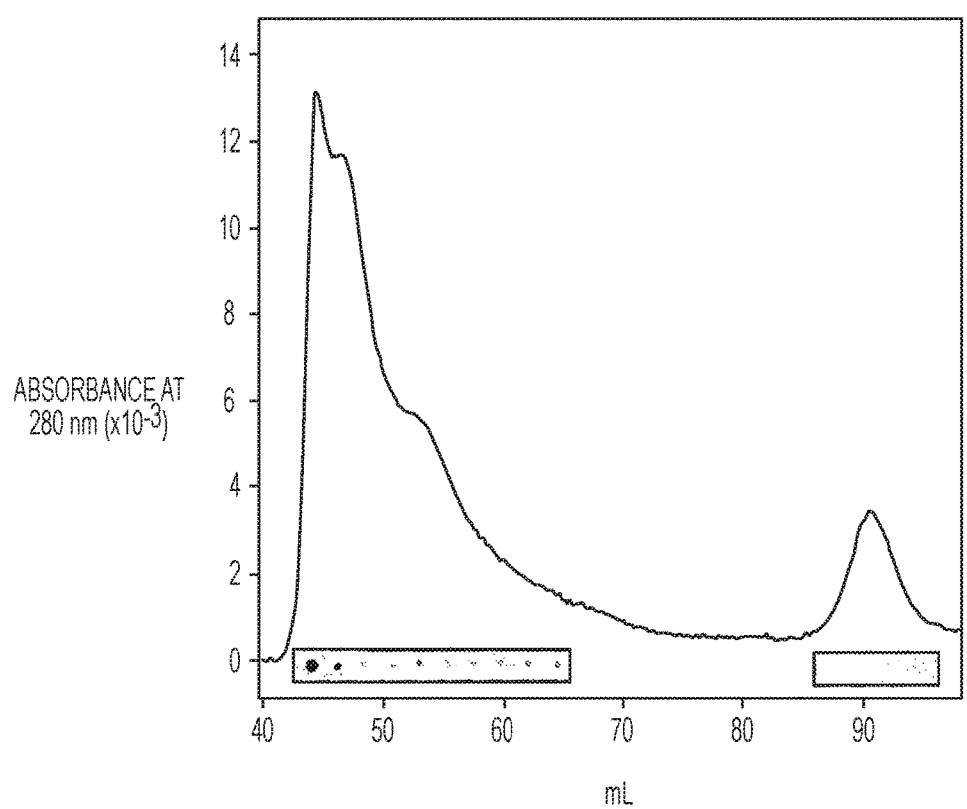
FIG. 9 represents an SEC elution profile of approximately a 168 μM solution of Aβ(40) A21C/A30C peptide as high molecular-weight β-structured oligomer. The insets below the two peaks represent dot blots of the fractions (evenly distributed throughout the peaks) assayed for A11 antibody binding capability.

FIG. 9 shows a SEC run of a 1 ml Aβ(40) A21C/A30C peptide solution of isolated and concentrated (to approximately 168 μM) oligomer obtained as in Example 5. SEC was carried out as in Example 3, using a Superdex 75 16/60 column (GE Healthcare) run at 1 ml min$^{-1}$. Under these conditions the sample elutes partly in the void volume (approximately 42 ml for this column, corresponding to >100 kDa proteins) and as high molecular-weight oligomers (corresponding to approximately 87 kDa proteins). A smaller fraction also elutes as a 7-8 kDa protein.

All fractions of the earlier peak and of the later peak were assayed for A11 (Biosource) binding according to the manufacturer's instructions. 3 μl of each fraction was dot blotted on an Immobilion-P$^{SQ}$ polyvinylidene fluoride (PVDF) membrane (Millipore) and allowed to dry. The membrane was then blocked over night (approximately 14 h) in 4° C. in 10% non-fat dry milk dissolved in 20 mM Tris-HCl, 140 mM NaCl, 0.01% Tween 20, pH 7.4 (TBST buffer). The membrane was then washed three times with TBST buffer for five minutes, and the A11 primary antibody (Biosource) at 0.5-0.8 μg ml$^{-1}$ in 5% non-fat dry milk dissolved in TBST buffer was applied to the membrane for 1 h at room temperature (21° C.). After washing away unbound antibody three times with TBST buffer for five minutes, the secondary antibody (a donkey ECL™ anti-rabbit IgG horseradish peroxidase conjugate from GE Healthcare) at 0.1 µg ml$^{-1}$ in 5% non-fat dry milk dissolved in TBST buffer was added to the membrane for 45-60 min at room temperature (21° C.). After washing away unbound antibody as above, SuperSignal West Pico chemiluminescent substrate (Pierce) was added according to the manufacturer's instructions, and horseradish peroxidase enzyme activity was detected by a CCD camera (Fujifilm LAS-1000) coupled to a dark box. As shown in FIG. 9, detection is strongest in the fraction appearing the earliest, thus corresponding to the largest of the high molecular-weight oligomeric species, whereas the 7-8 kDa peak does not react with the A11 antibody.

Figure 10A:
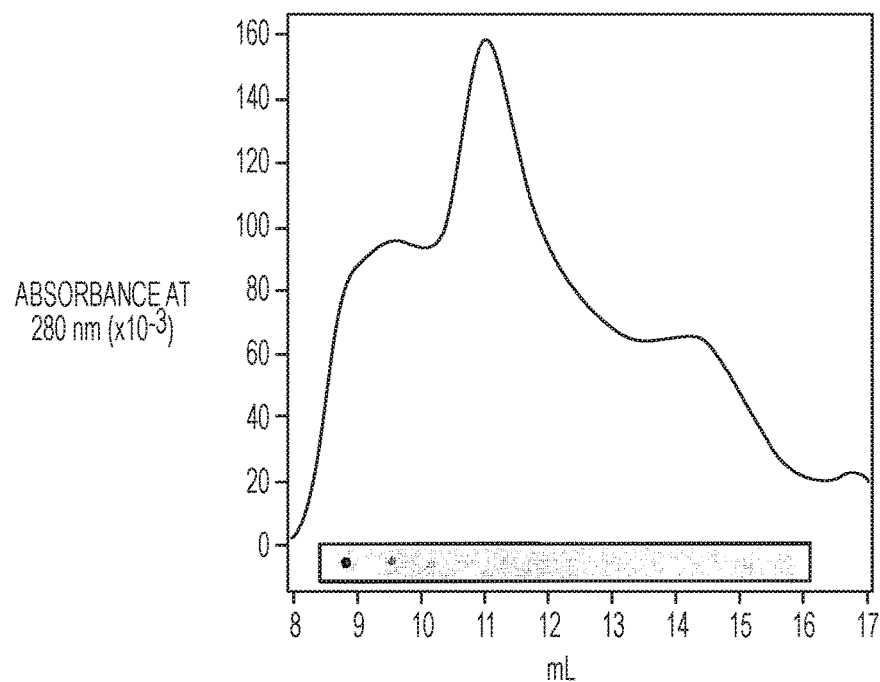
FIG. 10A represents an SEC elution profile of a concentrated solution (at approximately 800 μM) of Aβ(40) A21C/A30C peptide denatured in 6 M GdmCl prior to SEC. The inset below the profile represents a dot blot of the fractions (evenly distributed throughout the peaks) assayed for A11 antibody binding capability.
Figure 10B:
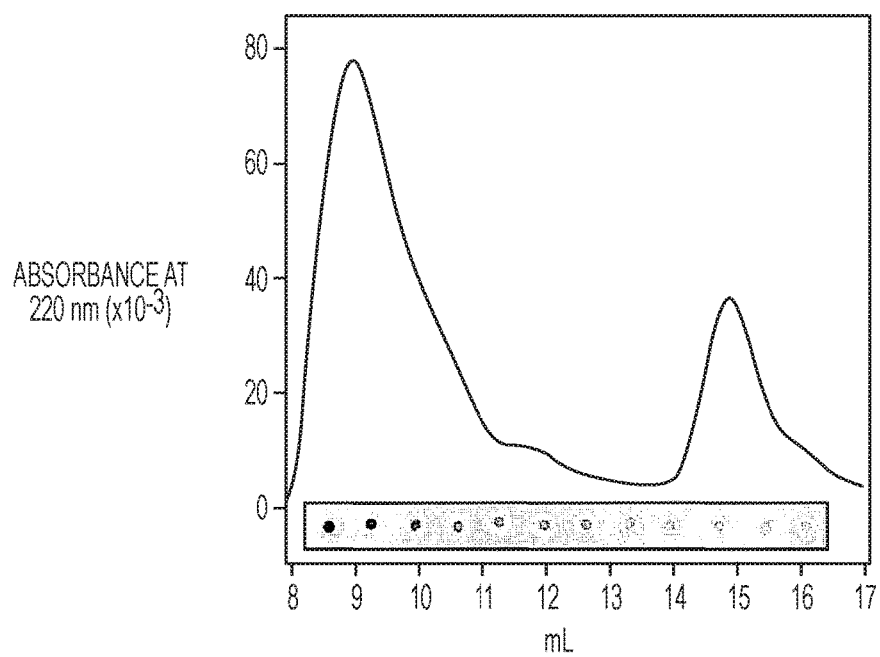
FIG. 10B represents an SEC elution profile of the first fraction in FIG. 10A that had the highest A11 affinity. The inset below the profile represents a dot blot of the fractions (evenly distributed throughout the peaks) assayed for A11 antibody binding capability.

In a similar experiment shown in FIG. 10A, 500 µl of an approximately 800 µM Aβ(40) A21C/A30C peptide solution in 6 M GdmCl, 50 mM K$^+$ phosphate, 50 mM NaCl, pH 7.2, was applied to a Superdex 75 10/300 column (GE Healthcare), and the fractions blotted as above. Again, the A11 antibody reacts with the larger of the oligomeric species with β structure. However, it does not recognize the coil oligomers. The first fraction that had the highest A11-binding capacity contained approximately 20 µM of Aβ(40) A21C/A30C peptide. This fraction was incubated for 16 h at 4° C. and then reanalyzed on the same column, yielding the elution profile shown in FIG. 10B which was also assayed for A11-binding capability. As above, the A11 antibody has a higher reactivity towards the larger of the oligomeric species. FIG. 10B also demonstrates that the formation of oligomers with β structure is at least partly reversible, and that they are relatively stable once formed (in analogy with the aggregation assay in FIG. 8).

Example 7. Coil- to β-Transition in Aβ(40) A21C/A30C

Figure 11A:
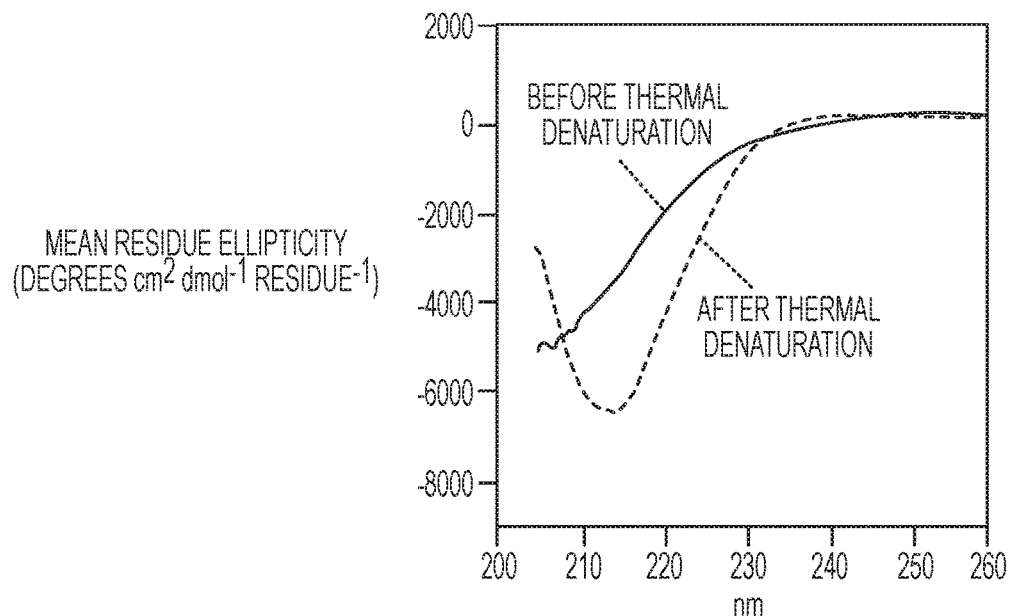
FIG. 11A represents far-UV CD spectra of the Aβ(40) A21C/A30C peptide as a coil-like protein at high concentration (1.1 mM), and its transformation to β-structured protein after thermal denaturation from 20° C. to 80° C. and back to 20° C. with a temperature slope of 2° C. min$^{-1}$.
Figure 11B:
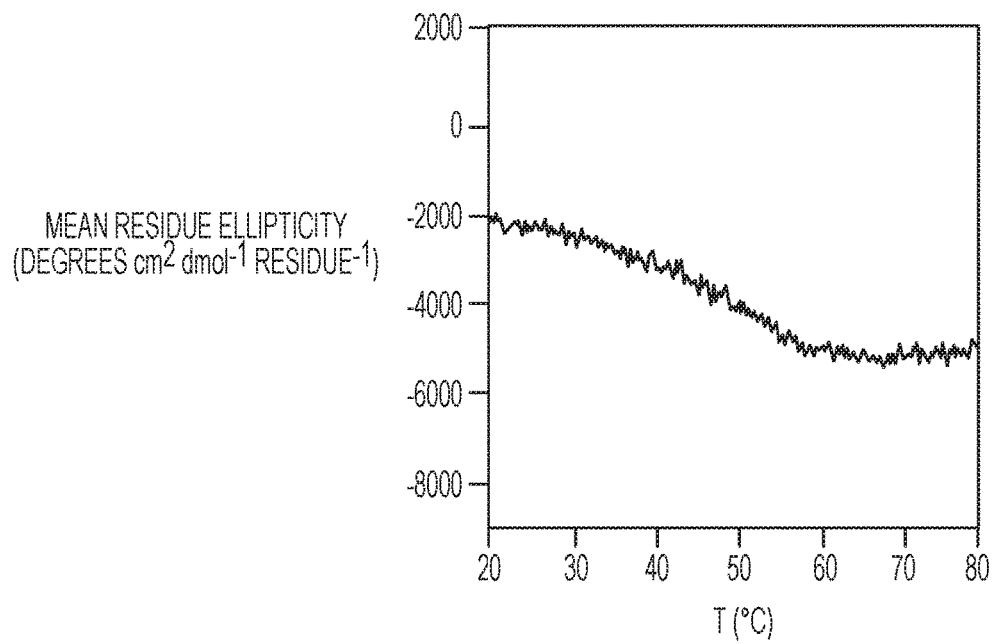
FIG. 11B shows the thermal denaturation profile described in FIG. 11A as monitored at 220 nm. There was no amorphous or fibrillar aggregation present in this sample neither before nor after thermal denaturation.

The transition from coil- to β-structure is intimately related to the oligomerization and fibrillization of the wild-type Aβ peptide, and to its toxicity. At solutions of 20-100 µM Aβ peptide at 4° C., this transition occurs spontaneously within 24 hours for Aβ(42) and days for Aβ(40) (Stine, W. B., et al., *J. Biol. Chem.* 278: 11612-11622 (2003)). For the Aβ(40) A21C/A30C peptide, this structural transition can be accelerated by heat without fibrillogenesis occurring. FIG. 11A shows the two CD spectra of a 1.1 mM Aβ(40) A21C/A30C peptide before (coil structure) and after (β structure) being denatured by a 2° C. min$^{-1}$ gradient of increasing temperature from 20 to 80° C. and back again. The transition is shown in FIG. 11B as monitored at 220 nm. In Example 8 below, it is demonstrated that the β structures thus formed are protofibrillar-like. Protofibrils are believed by many to be precursors of fibrils (e.g. Walsh, D. M., et al., *J. Biol. Chem.* 274: 25945-25952 (1999)). It should be noted that this sample did not exhibit any amorphous precipitation or fibrils even after this harsh treatment and at this concentration. This resilience towards fibrillogenesis is unprecedented for all derivatives of the Aβ peptide.

Example 8. TEM Analysis of Aβ(40) A21C/A30C Coil- and β-Structured Oligomers, and Protofibrillar-Like Species TEM images were obtained by a LEO 912 AB OMEGA electron microscope (Carl Zeiss SMT AG) equipped with a MegaView CCD camera (Olympus). Negative staining with uranyl acetate was used in all samples. Formvar/carbon coated nickel grids were activated with UV-light for 5 minutes, after which 5-10 µl of protein sample was applied to each grid for 2 minutes. Two steps of washing with approximately 10 µl of filtered deionized H$_2$O preceded the staining. A two-minute treatment with 2% uranyl acetate solution in filtered deionized H$_2$O completed the preparation of the grids, which were allowed to air dry for a few minutes before storage or immediate analysis.

Figure 12A:
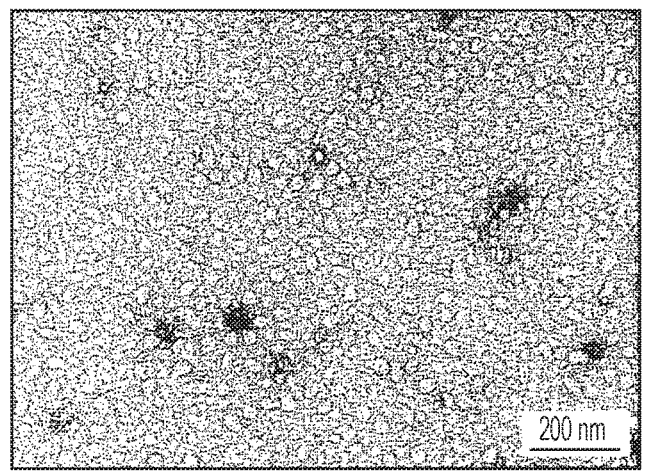
FIG. 12A represents transmission electron microscope (TEM) images of a negatively stained (uranyl acetate) solution of coil-like oligomers of Aβ(40) A21C/A30C peptide, which was approximately 500 μM at the time of grid application. The spherical structures are 15-35 nm in diameter.
Figure 12B:
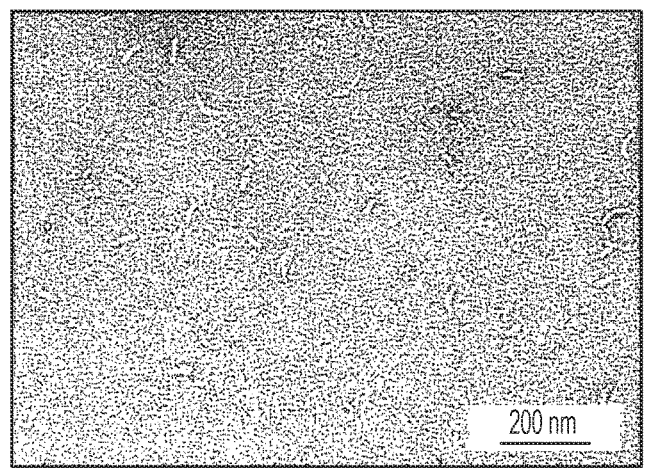
FIG. 12B represents TEM images of the same solution as in FIG. 12A incubated at 60° C. for 20 min prior to grid application. The protofibrillar-like structures are 6-7 nm in width and on average approximately 36 nm in length.
Figure 12C:
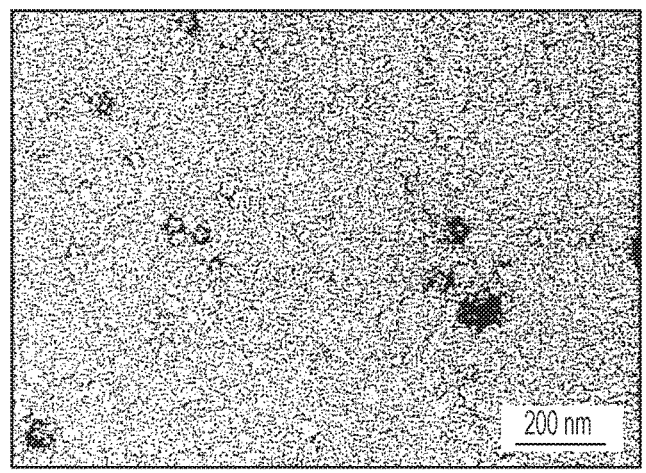
FIG. 12C represents TEM images of a similarly negatively stained solution of approximately 150 μM Aβ(40) A21C/A30C as a β-structured high molecular-weight oligomer. The spherical structures are similar to those in FIG. 12A, having diameters of 15-35 nm. The scale bar is 200 nm in these figures.

In FIG. 12A, an approximately 500 µM solution containing Aβ(40) A21C/A30C in coil conformation was applied to the grids. In FIG. 12B, the same solution used to prepare the sample in FIG. 12A was denatured at 60° C. for 20 minutes prior to being applied to the grid. In FIG. 12C, an approximately 150 µM solution of Aβ(40) A21C/A30C oligomers with β structure (obtained as in Example 5) was analyzed.

The scale bar is 200 nm in FIG. 12. The spherical structures observed in FIG. 12A and FIG. 12C are similar in morphology and dimension to each other, having diameters of 15 nm to 35 nm. They are also similar to previously published TEM images that have used the same staining technique. These spherical structures of wild-type Aβ(40) peptide were recently observed for oligomers of Aβ(40) having β structure (Chimon. S., et al., *Nature Struct. Mol. Biol.* 14: 1157-1164 (2007)). In this publication, Chimon et al. claim that these structures are the toxic species.

The structures observed in FIG. 12B are protofibrillar-like, with an average dimension of 6-7 nm in width and approximately 36 nm in length (although the lengths vary). They are very similar in morphology and dimension to the wild-type Aβ(40) protofibrils, which have average widths of 6-10 nm and lengths of 5-160 nm (Walsh, D. M., et al., *J. Biol. Chem.* 272: 22364-22372 (1997)).

Example 9. Fibrillation Assay of Aβ(42) A21C/A30C

Figure 13:
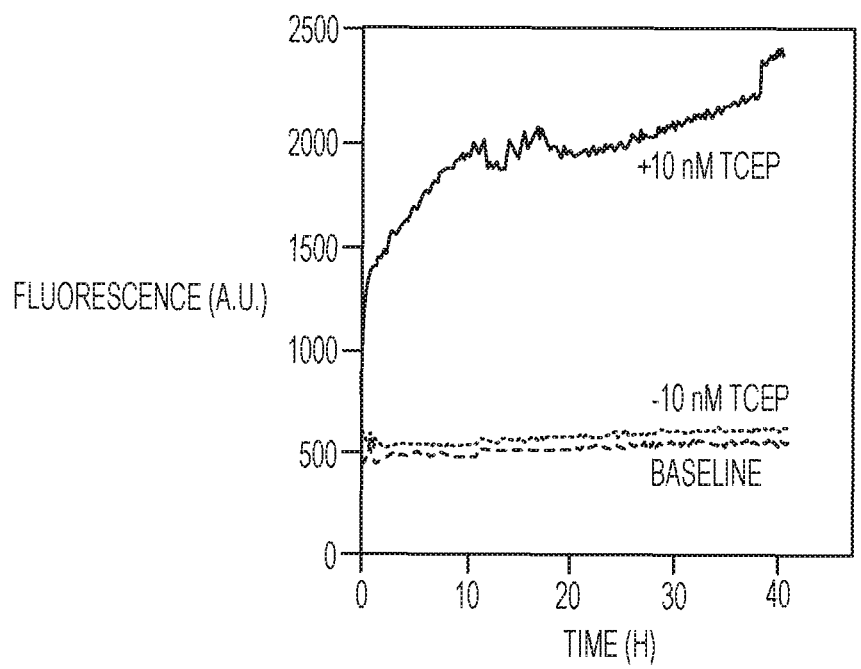
FIG. 13 represents a fibrillation assay of the Aβ(42) A21C/A30C peptide with formed and broken (by 10 mM TCEP) disulphide bonds at 117 μM. Fibrillation was monitored by TFT binding (10 μM) and the assays were carried out at 37° C. with shaking in phosphate buffer at pH 7.2.

The fibrillation assay was carried out as in example 2 with the exception that data points were recorded every 10 min. The concentration of Aβ(42) A21C/A30C was approximately 117 µM. The result is presented in FIG. 13.

Fibrillation of the reduced sample commences immediately, whereas the two oxidized samples remain non-fibrillized throughout the 42-h assay. This experiment demonstrates that the A21C/A30C disulphide bond is effective in preventing fibrillation also in the Aβ(42) derivative, which has a much higher inherent tendency to fibrillate compared to the Aβ(40) peptide.

Example 10. SEC Analysis of the Aβ(42) A21C/A30C with a Dot Blot of the Different Fractions Against the A11 Polyclonal Antibody The SEC was carried out on a Sephacryl S300 16/60 column as in example 5, and the dot blot was carried out as in example 6. The result is presented in FIG. 14.

Figure 7A:
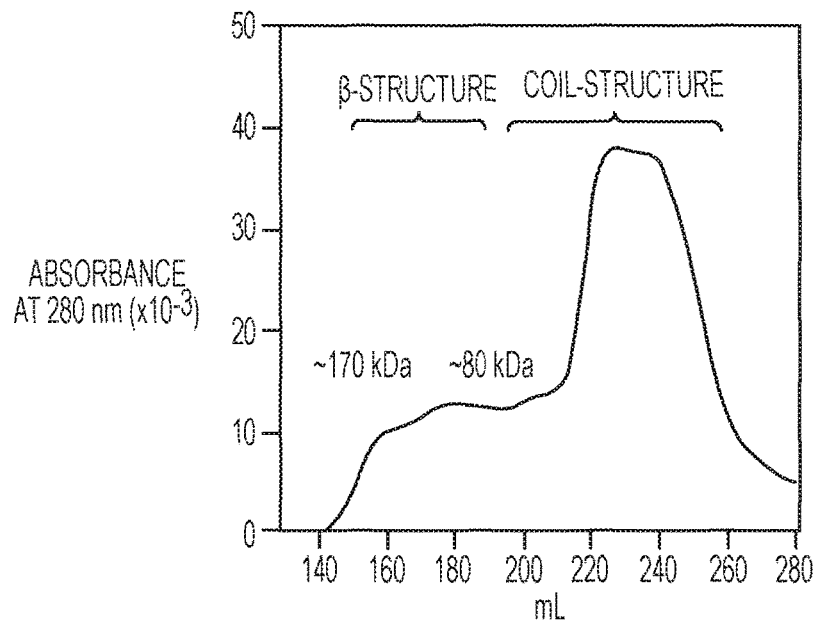
FIG. 7A represents an SEC elution profile of a concentrated solution (at approximately 1.7 mM) of Aβ(40) A21C/A30C peptide that was denatured in 6M GdmCl prior to SEC. The peptide elutes as high molecular-weight oligomers with β structure, and as low molecular-weight oligomers and monomeric protein with coil structure.
Figure 7B:
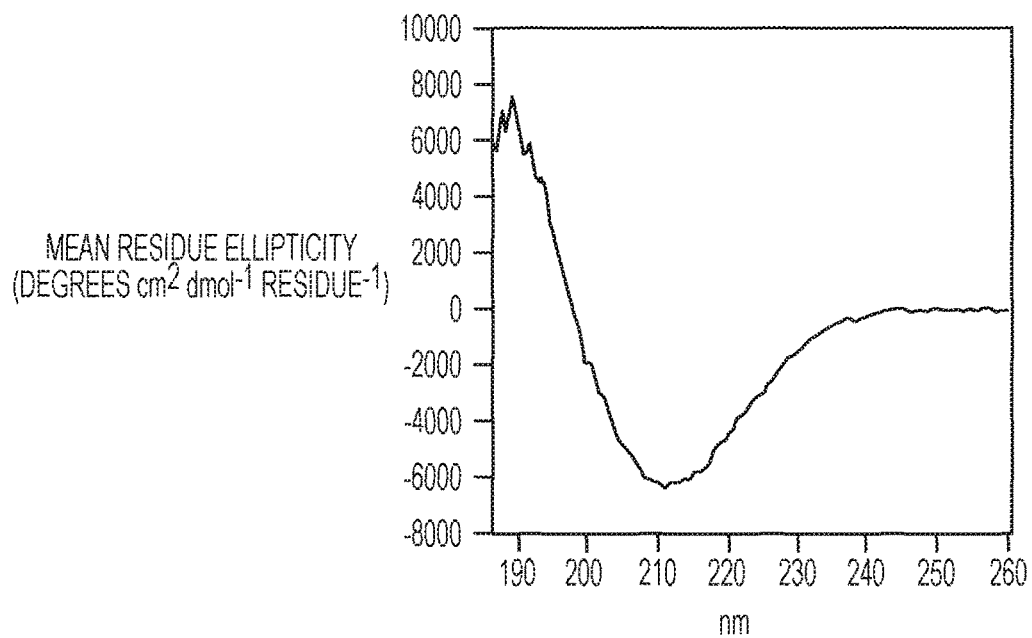
FIG. 7B represents a far-UV CD spectrum of 250 μM Aβ(40) A21C/A30C peptide as a β-structured peptide oligomer. This spectrum is virtually identical for all preparations of said peptide with β structure, including protofibrillar states.
Figure 14:
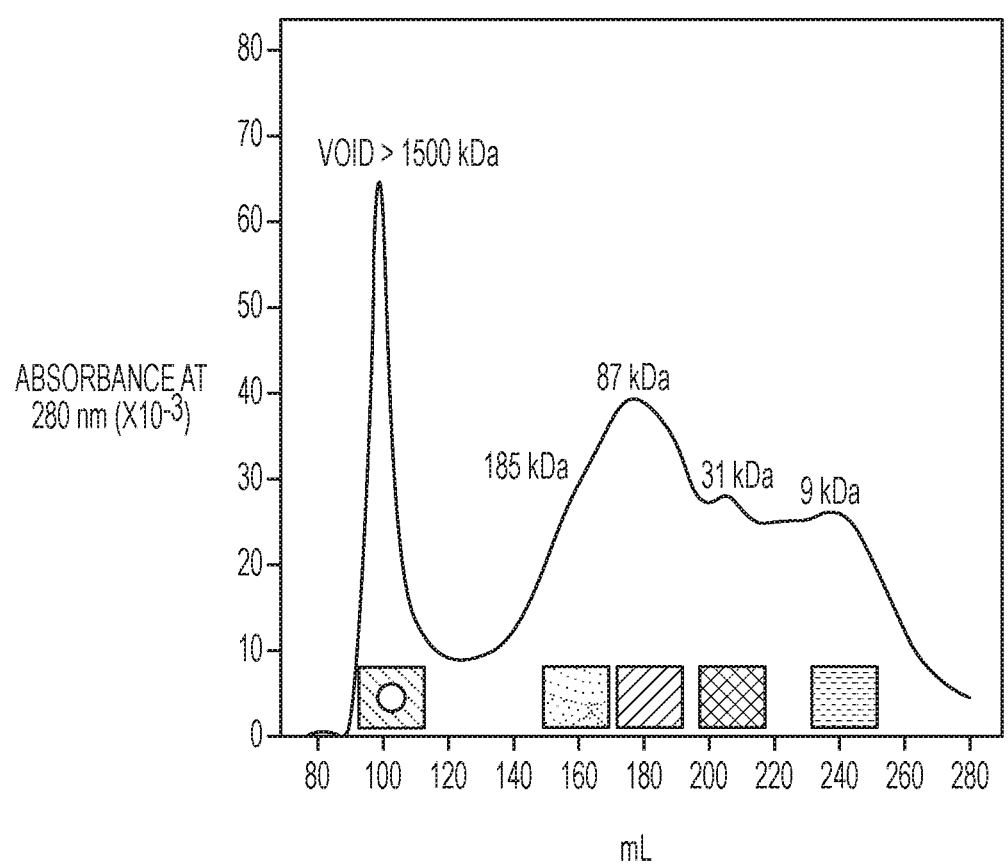
FIG. 14 represents an SEC elution profile of a concentrated solution of Aβ(42) A21C/A30C peptide that was denatured in 6M GdmCl prior to SEC. The insets below the chromatogram represents dot blots of the fractions (the amount of sample applied to the membrane was normalized according to the absorbance at 280 nm) assayed for A11 antibody binding capability.

Comparing the chromatogram in FIG. 14 with the chromatogram in FIG. 7A for the Aβ(40) A21C/A30C peptide demonstrates that the Aβ(42) A21C/A30C peptide has a higher tendency to oligomerize into high molecular-weight oligomers. But the oligomeric forms of both Aβ(42) A21C/A30C and Aβ(40) A21C/A30C peptides have similar sizes. The A11-binding species elutes in the void on this column which has a cutoff of approximately ≥1500 kDa.

Example 11. Stability of the A11-Binding Epitope

Figure 15A:
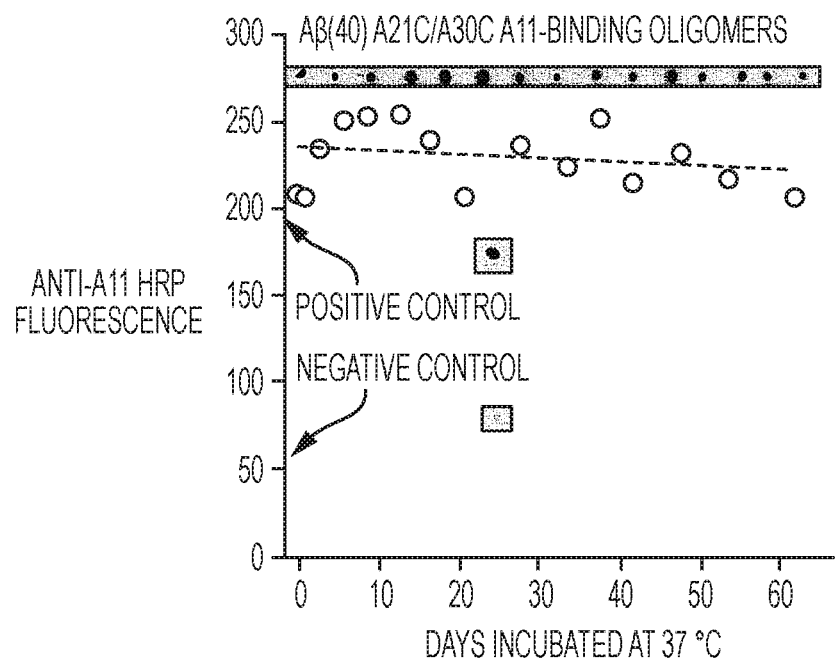
FIG. 15A represents a time-dependent assay of a 80 kDa Aβ(40) A21C/A30C SEC fraction that was concentrated to 20 μM and incubated at 37° C. Time points were taken and assayed for the presence of the A11 epitope.

A 80-kDa fraction of Aβ(40) A21C/A30C peptide obtained as in example 5 was concentrated to 20 µM and incubated at 37° C. in 50 mM K⁺ phosphate buffer, 50 mM NaCl, and 0.05% azide. Samples were removed at regular intervals during a two-month period and stored at −24° C. until analysis. The dot blot was carried out as in example 6, and the result is presented in FIG. 15A. The A11 epitope formed quickly already during the concentration step, and remained stable during the full course of the experiment (for approximately 60 days). The fluorescence intensity decreased with only 0.1% per day.

A related experiment on a monomeric fraction of Aβ(40) A21C/A30C peptide obtained from the same SEC as above was concentrated to 90 μM and incubated at 37° C. in 50 mM K⁺ phosphate buffer, 50 mM NaCl, and 0.05% azide. Samples removed at the same intervals as above during a two-month period did not exhibit any A11 binding (not shown).

Figure 15B:
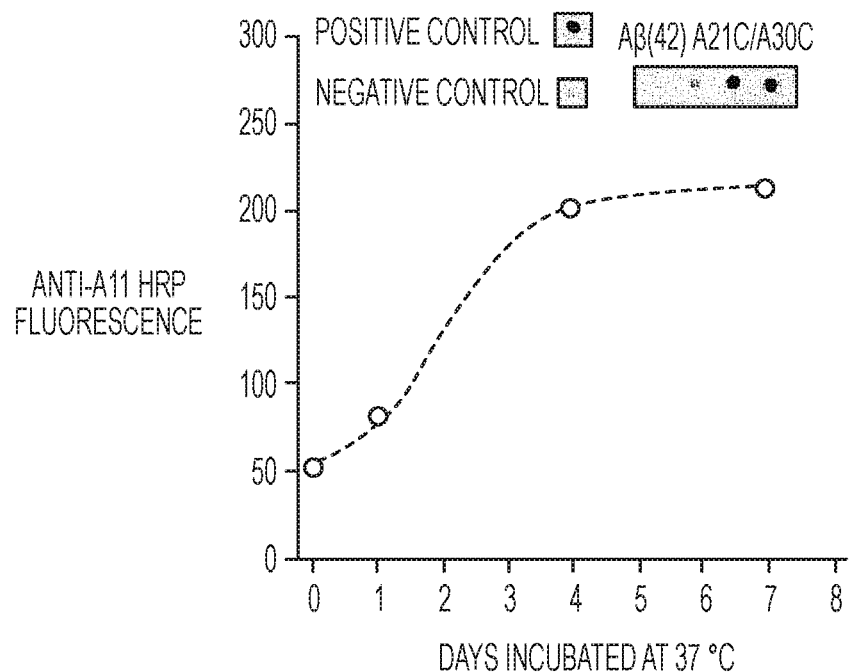
FIG. 15B represents a time-dependent assay of a 10 kDa Aβ(42) A21C/A30C SEC fraction that was concentrated to 50 μM and incubated at 37° C. Time points were taken and assayed for the presence of the A11 epitope.

A similar sample of monomeric Aβ(42) A21C/A30C peptide obtained as in example 5 and concentrated to 50 μM was incubated at 37° C. in 50 mM K⁺ phosphate buffer, 50 mM NaCl, and 0.05% azide was probed for A11 binding. This sample displayed the A11 epitope already after a few days (FIG. 15B). Once nucleated, the oligomerization into the high molecular weight oligomers occurred with a $t_{1/2}$ of 2.2 days in this experiment.

Taken together, these experiments demonstrate that the high molecular weight oligomers are formed spontaneously in the Aβ(42) A21C/A30C peptide whereas the shorter Aβ(40) A21C/A30C peptide is more resilient towards the conformational change into β structure that is intimately associated with oligomerization into the high molecular-weight oligomers. Once formed, the A11 binding oligomers are remarkably stable, again demonstrating the ability of the invention to arrest the fibrillation step completely.

The invention claimed is:

1. A method of immunization for reducing toxic damage caused by oligomeric forms of the amyloid-β protein in a mammal, said method comprising administering to said mammal a therapeutically effective amount of a peptide as immunogen to raise an immune response in said mammal against toxic oligomeric forms of the amyloid-β protein, said peptide comprising: the amino acid sequence L-V-F-F-C (SEQ ID NO: 13) corresponding to amino acids 17 to 21 of SEQ ID NO: 4 and the amino acid sequence C-I-I-G-L-M-V (SEQ ID NO: 14) corresponding to amino acids 30 to 36 of SEQ ID NO: 4; exactly two cysteines corresponding to Cys21 and Cys30 in SEQ ID NO: 4; and exactly one disulfide bond, said exactly one disulfide bond is between said two cysteines corresponding to Cys21 and Cys30 in SEQ ID NO: 4, wherein said peptide is resistant towards fibrillogenesis.

2. The method according to claim 1, wherein said peptide comprises the amino acid sequence L-V-F-F-C-E-D-V-G-S-N-K-G-C-I-I-G-L-M-V (SEQ ID NO: 16) corresponding to amino acids 17 to 36 of SEQ ID NO: 4.

3. The method according to claim 2, wherein said peptide comprises the amino acid sequence corresponding to amino acids 1 to 40 of SEQ ID NO: 4.

4. The method according to claim 3, wherein said peptide comprises the amino acid sequence of SEQ ID NO: 4.

5. The method according to claim 2, wherein said peptide comprises a glycine substitution at the position corresponding to amino acid 22 in SEQ ID NO: 4.

6. The method according to claim 1, wherein said peptide comprises a methionine sulphoxide residue substitution at the position corresponding to amino acid 35 in SEQ ID NO: 4.

7. The method according to claim 1, wherein one or two terminal amino acids of said peptide have been maleimidated.

8. The method according to claim 1, wherein the N-terminal amino acid of said peptide has been acetylated.

9. The method according to claim 1, wherein the C-terminal amino acid of said peptide has been amidated.

* * * * *